US008846409B2

(12) United States Patent
Flockhart et al.

(10) Patent No.: US 8,846,409 B2
(45) Date of Patent: Sep. 30, 2014

(54) METHODS OF PREPARING CANNABINOIDS FROM PLANT MATERIAL

(75) Inventors: Ian R. Flockhart, Hull (GB); Gary William Wheatley, Kingswood (GB); Su Dring, Hull (GB); Leslie Archer, Hull (GB)

(73) Assignee: GW Pharma Limited, Salisbury (GB)

( * ) Notice: Subject to any disclaimer, the term of this patent is extended or adjusted under 35 U.S.C. 154(b) by 464 days.

(21) Appl. No.: 12/714,907

(22) Filed: Mar. 1, 2010

(65) Prior Publication Data

US 2010/0168448 A1 Jul. 1, 2010

Related U.S. Application Data

(63) Continuation of application No. 10/528,951, filed as application No. PCT/GB03/04078 on Sep. 23, 2003, now Pat. No. 7,700,368.

(30) Foreign Application Priority Data

Sep. 23, 2002 (GB) .................................. 0222077.0

(51) Int. Cl.
G01N 33/00 (2006.01)
C07D 311/80 (2006.01)
(52) U.S. Cl.
CPC .................................. C07D 311/80 (2013.01)
USPC .......................................... 436/177; 436/172
(58) Field of Classification Search
USPC .................................................. 436/177, 172
See application file for complete search history.

(56) References Cited

U.S. PATENT DOCUMENTS

| 6,365,416 | B1 | 4/2002 | Elsohly et al. |
| 6,403,126 | B1 | 6/2002 | Webster et al. |
| 6,946,150 | B2 * | 9/2005 | Whittle .......................... 424/725 |
| 7,025,992 | B2 | 4/2006 | Whittle et al. |
| 2002/0086438 | A1 | 7/2002 | Elsohly et al. |

FOREIGN PATENT DOCUMENTS

| EP | 2161262 A1 | 3/2010 |
| JP | 3153625 A | 7/1991 |
| WO | WO 02/32420 A1 | 4/2002 |
| WO | WO 02/064109 A1 | 8/2002 |
| WO | WO 03/063847 A | 8/2003 |
| WO | WO 03/064407 A3 | 8/2003 |

OTHER PUBLICATIONS

Lehmann T. et al., "A New Chromatographic Method for the Isolation of Levo-Delta-9-Trans Tetrahydrocannabinolic Acid A," *Phytochemical Analysis*, vol. 3, No. 2, pp. 88-90 (1992).
ODCCP, Bulletin on Narcotics, 1976, Issue 4—007, M. Reppeto et al., "Separation of Cannabinoids," pp. 69-74.
Paris M. R. et al., "Isolation of 2 Constituents Cannabidiolic-Acid and Tetra Hydro Cannabinolic-Acid From Cannabis-Sativa by Preparative Thin Layer Chromatography," *Annales pharmaceutiques françaises*, vol. 31, No. 3, 1973, pp. 186-188.

(Continued)

Primary Examiner — Sam P Siefke
(74) Attorney, Agent, or Firm — Wolf, Greenfield & Sacks, P.C.

(57) ABSTRACT

The invention relates to methods of preparing cannabinoids in substantially pure form starting from plant material. Also described are substantially pure preparations of various cannabinoids and cannabinoid acids, and also extracts enriched in cannabinoids and cannabinoid acids.

12 Claims, 21 Drawing Sheets

TLC profile of G1 chemovar starting material and purified THCA

(56) References Cited

OTHER PUBLICATIONS

R. Straight, et al., "Marihuana Extraction and Purification for Oral Administration of Known Amounts of $\Delta^9$-Tetrahydrocannabinol (THC)," *Biochemical Medicine*, vol. 8, pp. 341-344, 1973.

Gaoni, et al., "The Isolation and Structure of $\Delta^1$-Tetrahydrocannabinol and Other Neutral Cannabinoids from Hashish", *Journal of the American Chemical Society*, vol. 93: 217-224 (1971).

Merkus, Frans W.H.M., *Cannabivarin and Tetrahydrocannabivarin, Two New Constituents of Hashish*, Nature, vol. 232, pp. 579-580 (1971).

\* cited by examiner

Figure 1: TLC profile of G1 chemovar starting material and purified THCA
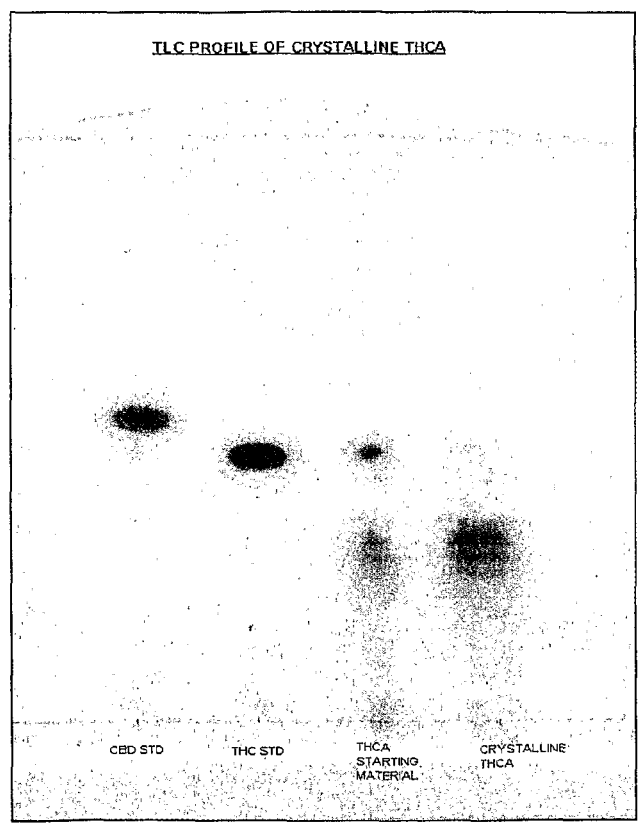

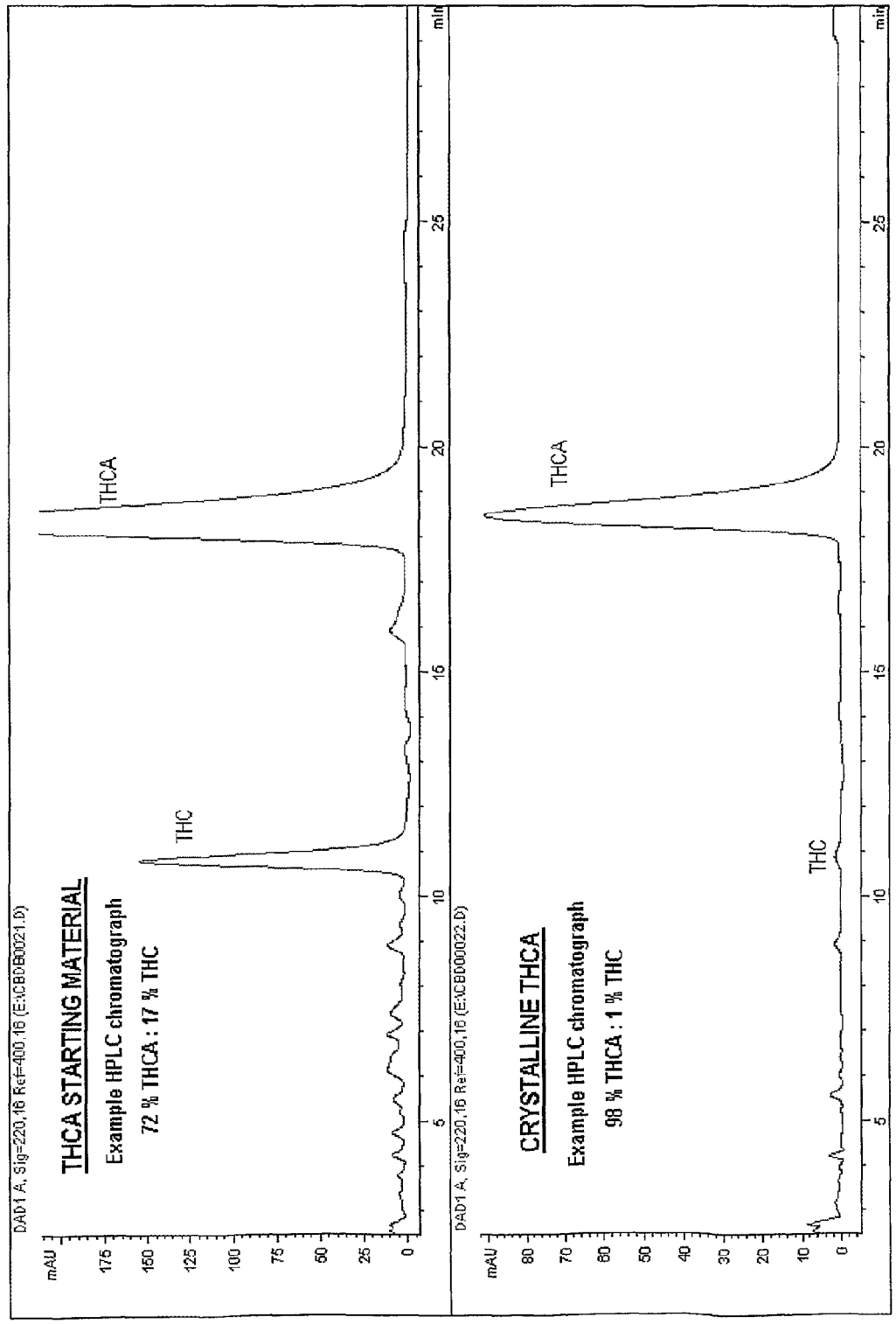
FIGURE 2: HPLC profiles of G1 chemovar starting material and purified d9 THCA

Figure 3: TLC profile of G5 chemovar starting material and purified CBDA
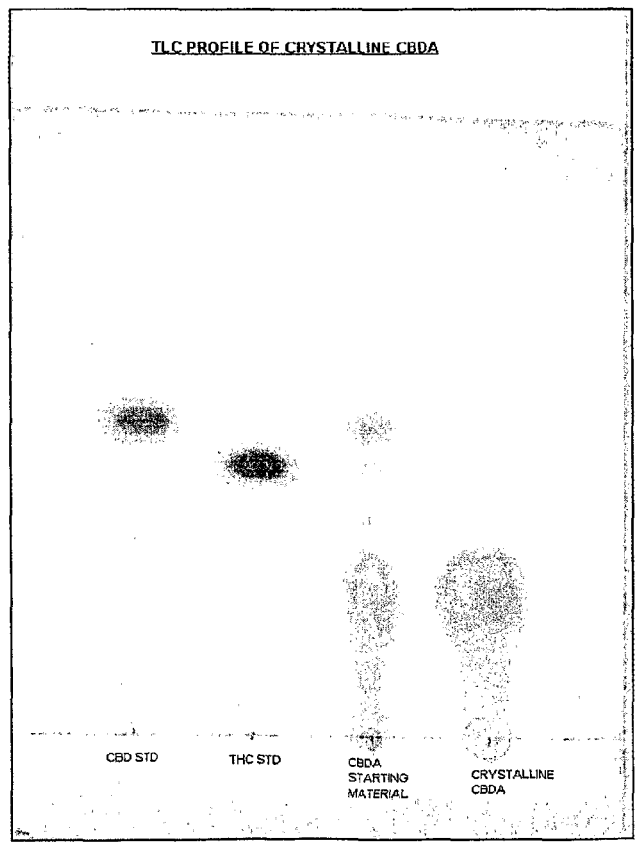

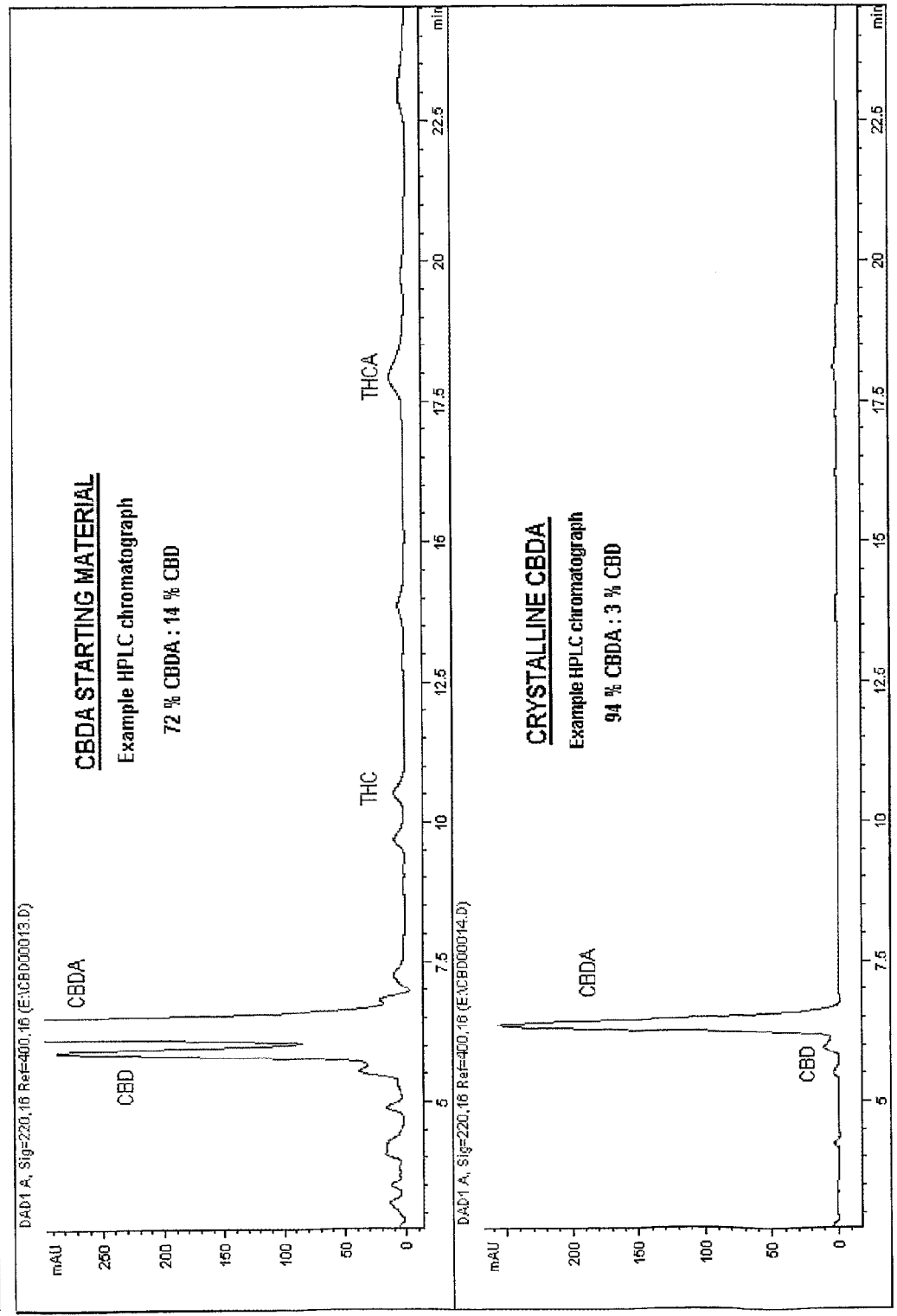

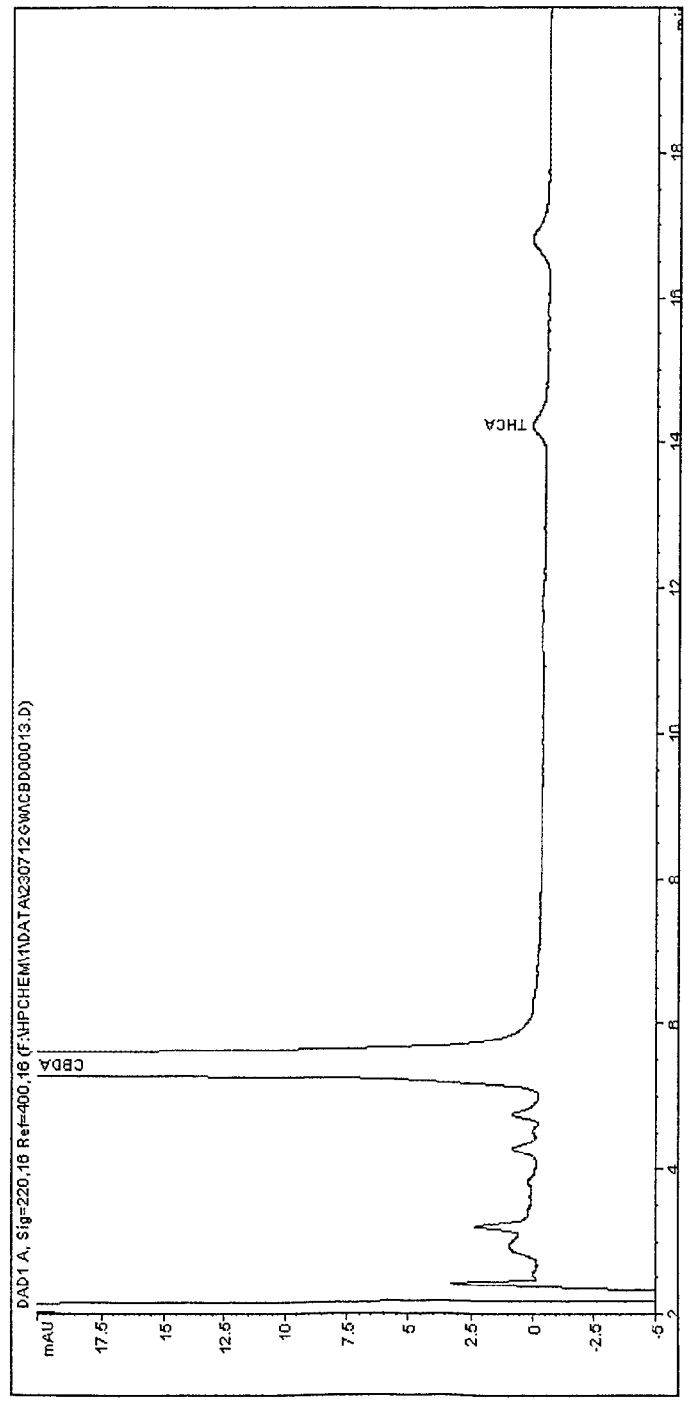
Figure 5 - HPLC profile of colourless CBDA

Figure 6: TLC profiles of BDS starting material and purified d9 THC
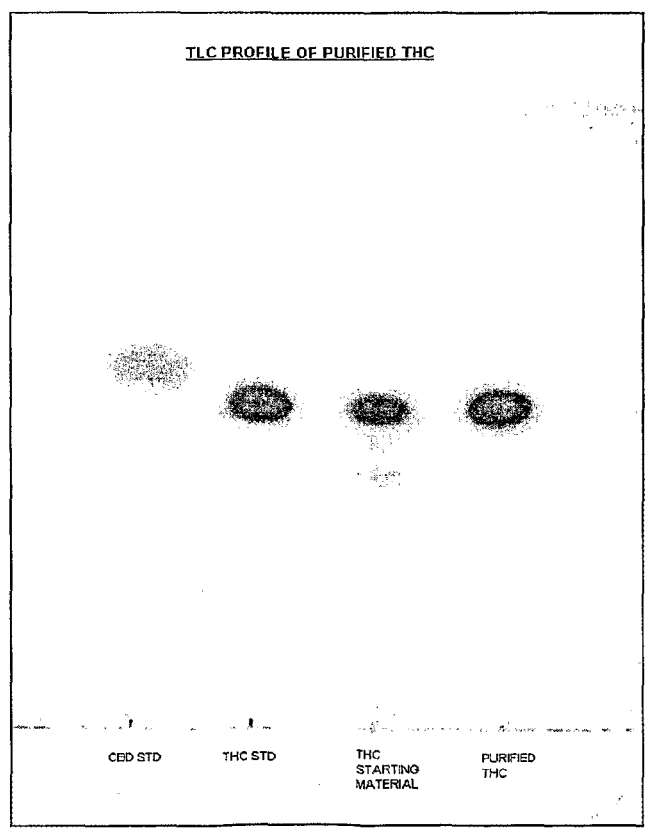

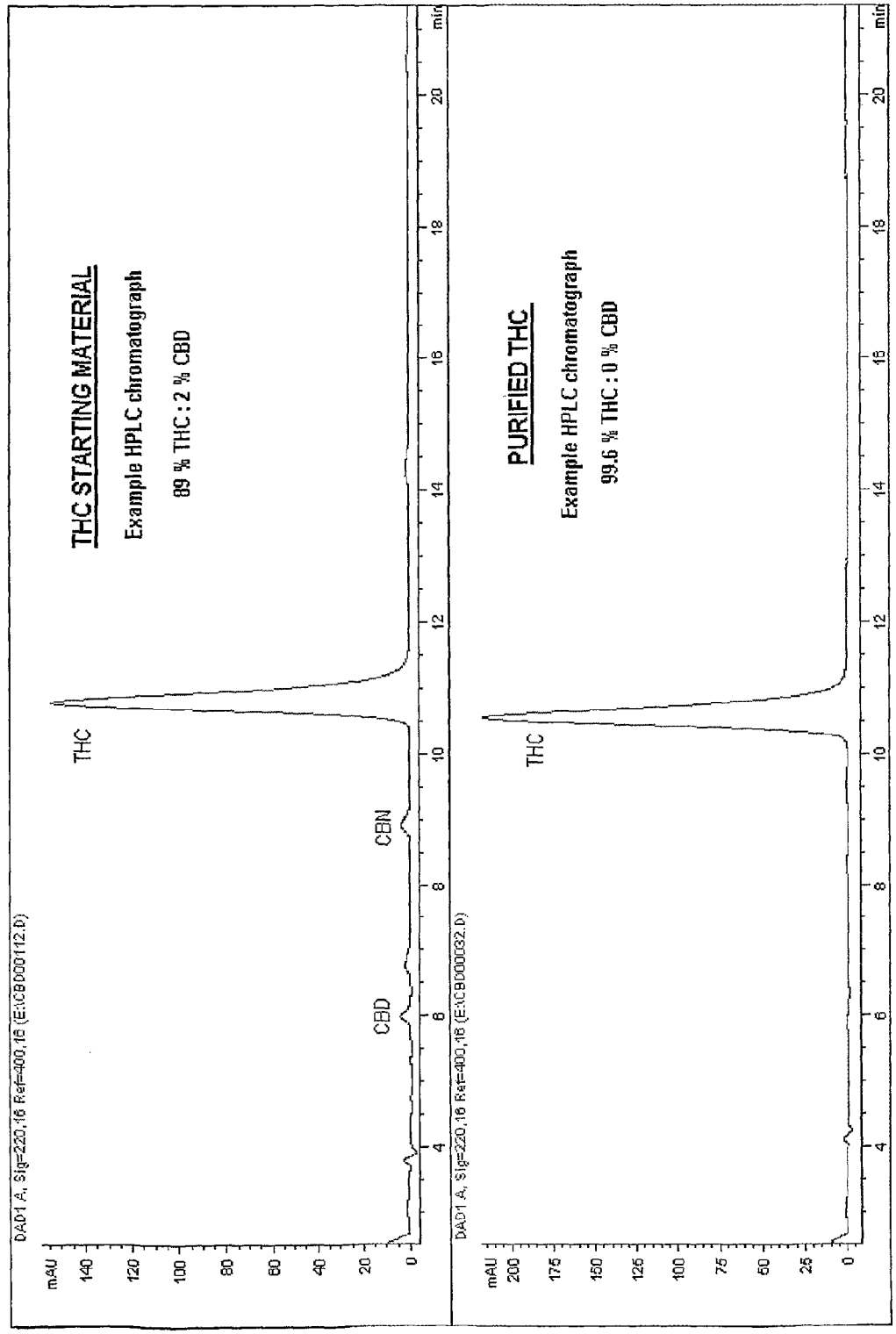

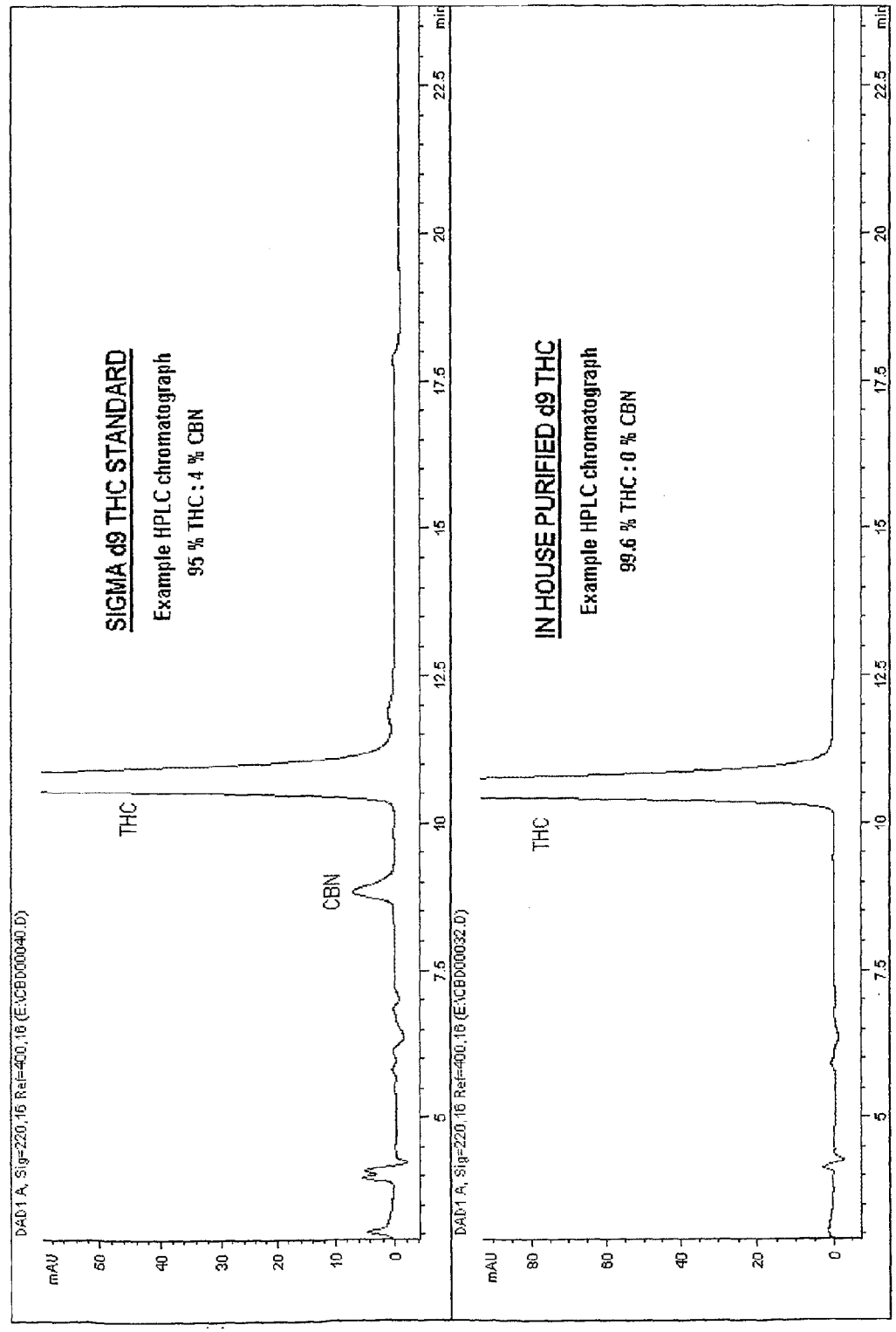

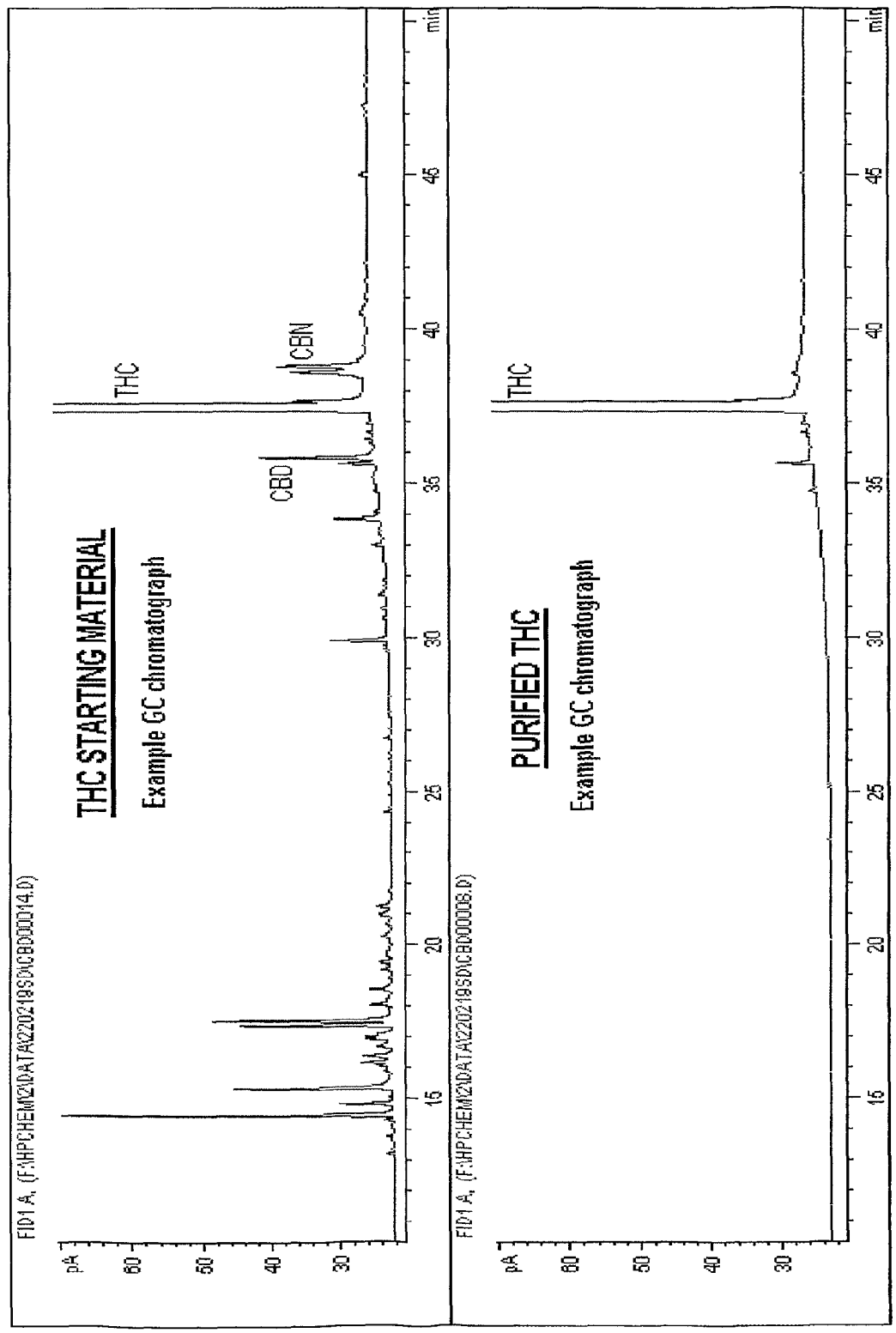
FIGURE 9: GC profiles of BDS starting material and purified d9 THC

Figure 10: TLC profiles of BDS starting material and purified d9 THCV
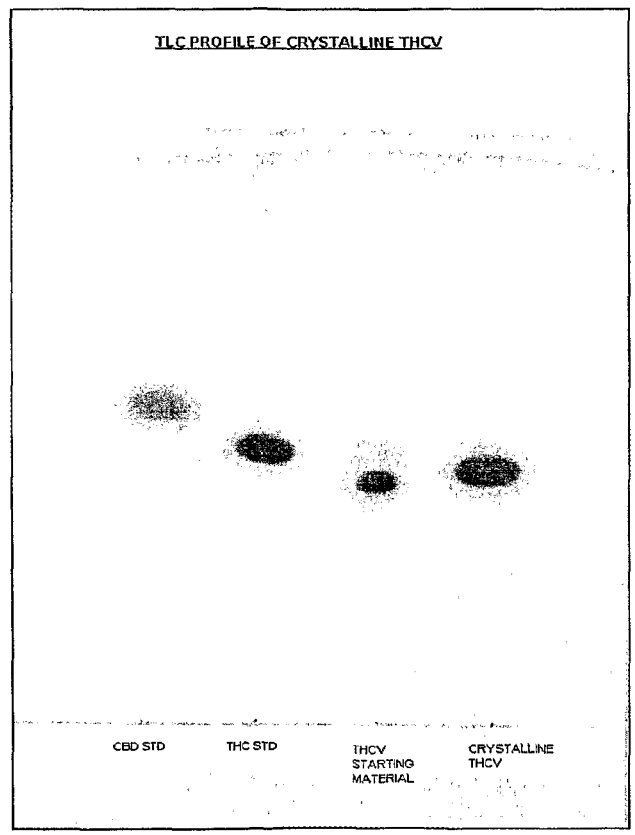

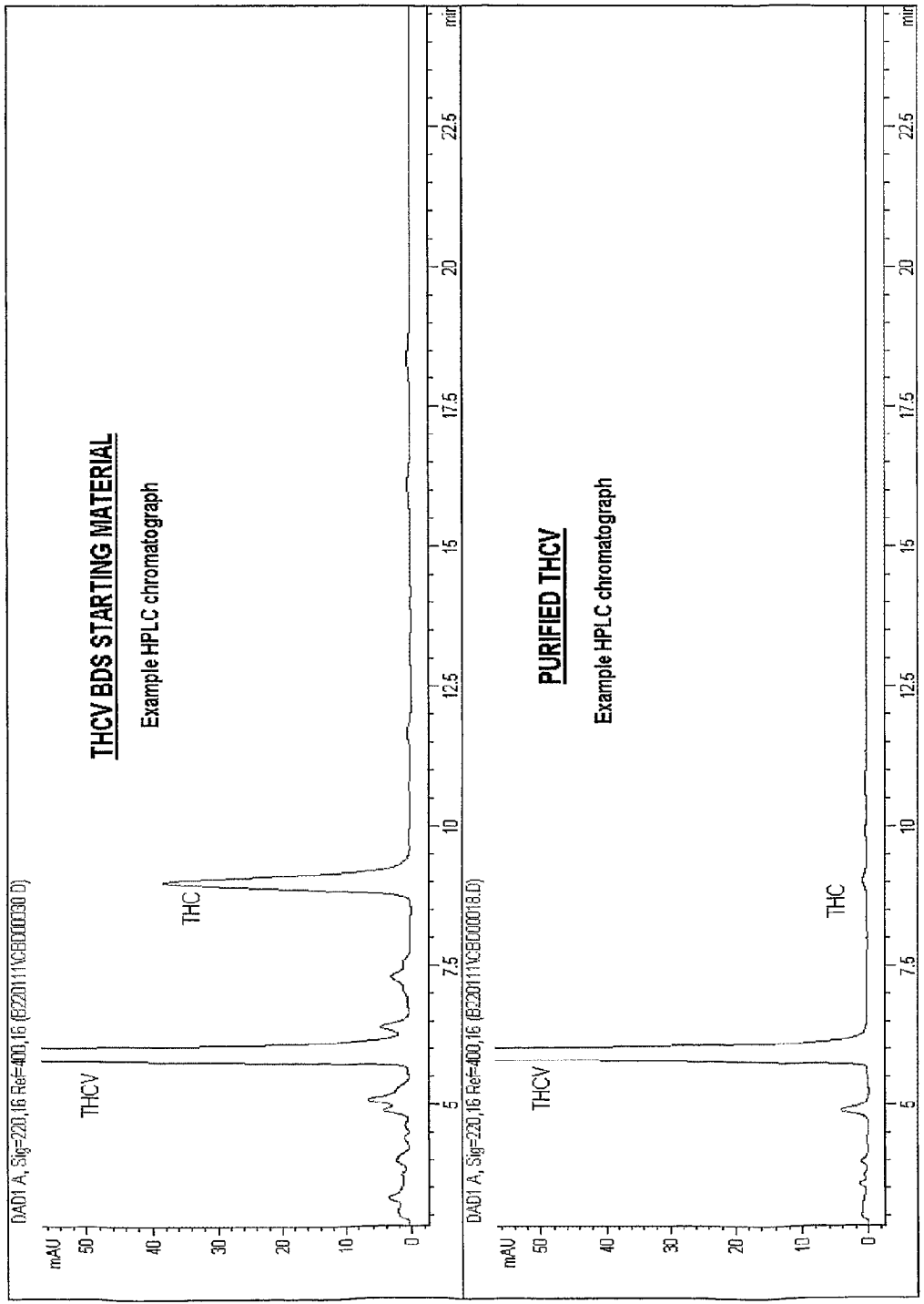
FIGURE 11: HPLC profiles of BDS starting material and purified d9 THCV

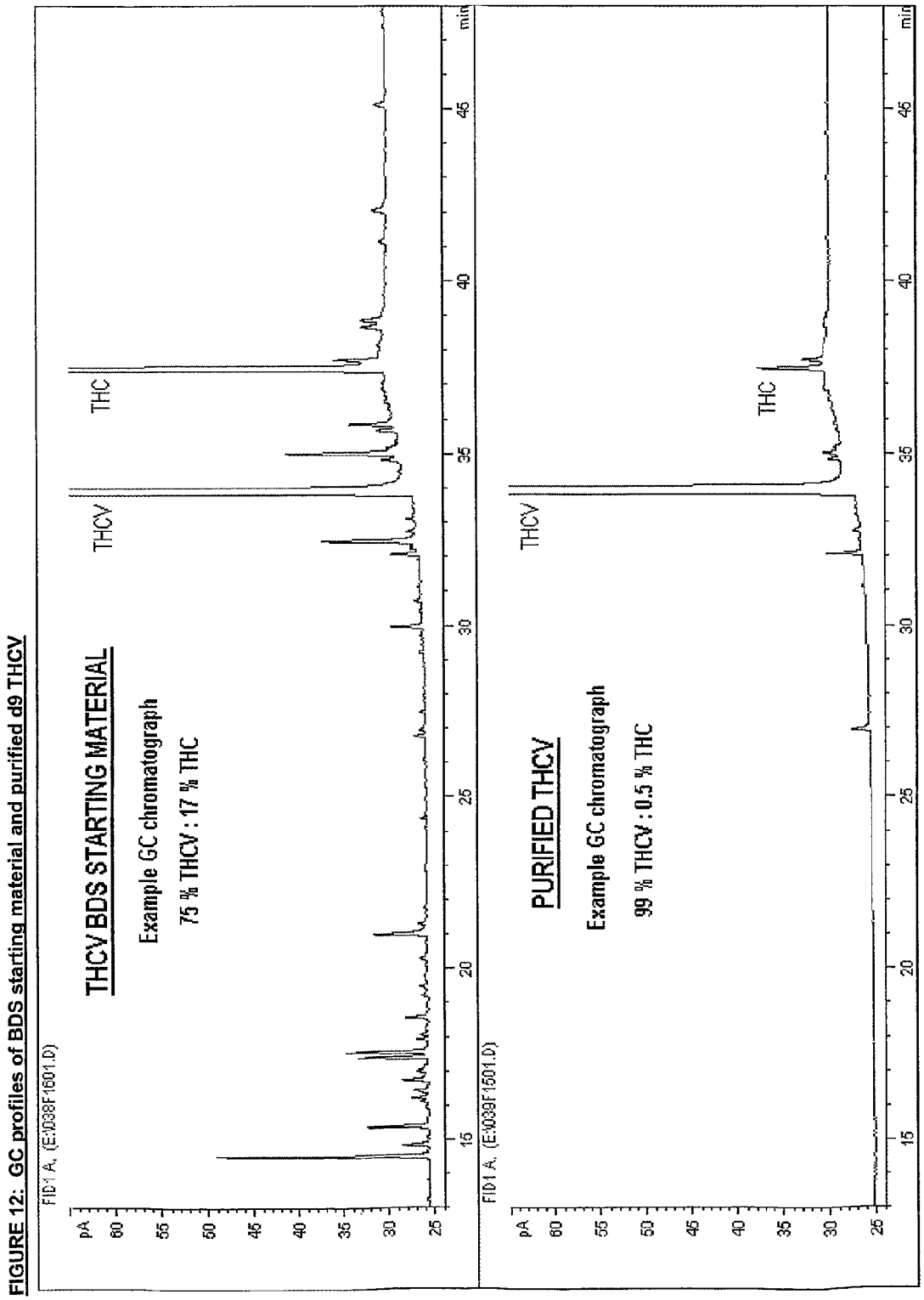

Figure 13: TLC profiles of G41chemovar starting material (post decarboxylation) and enriched CBG extract.
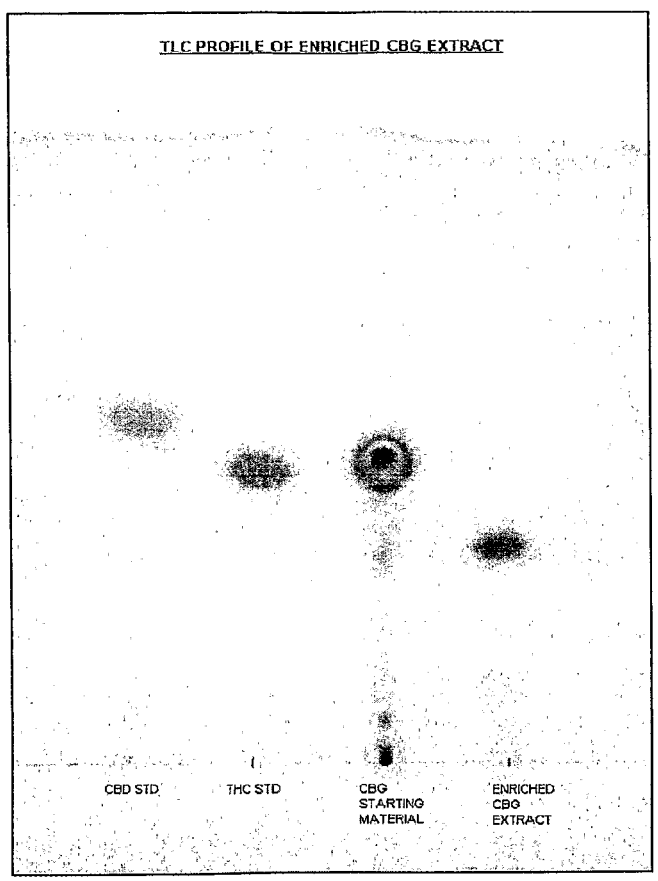

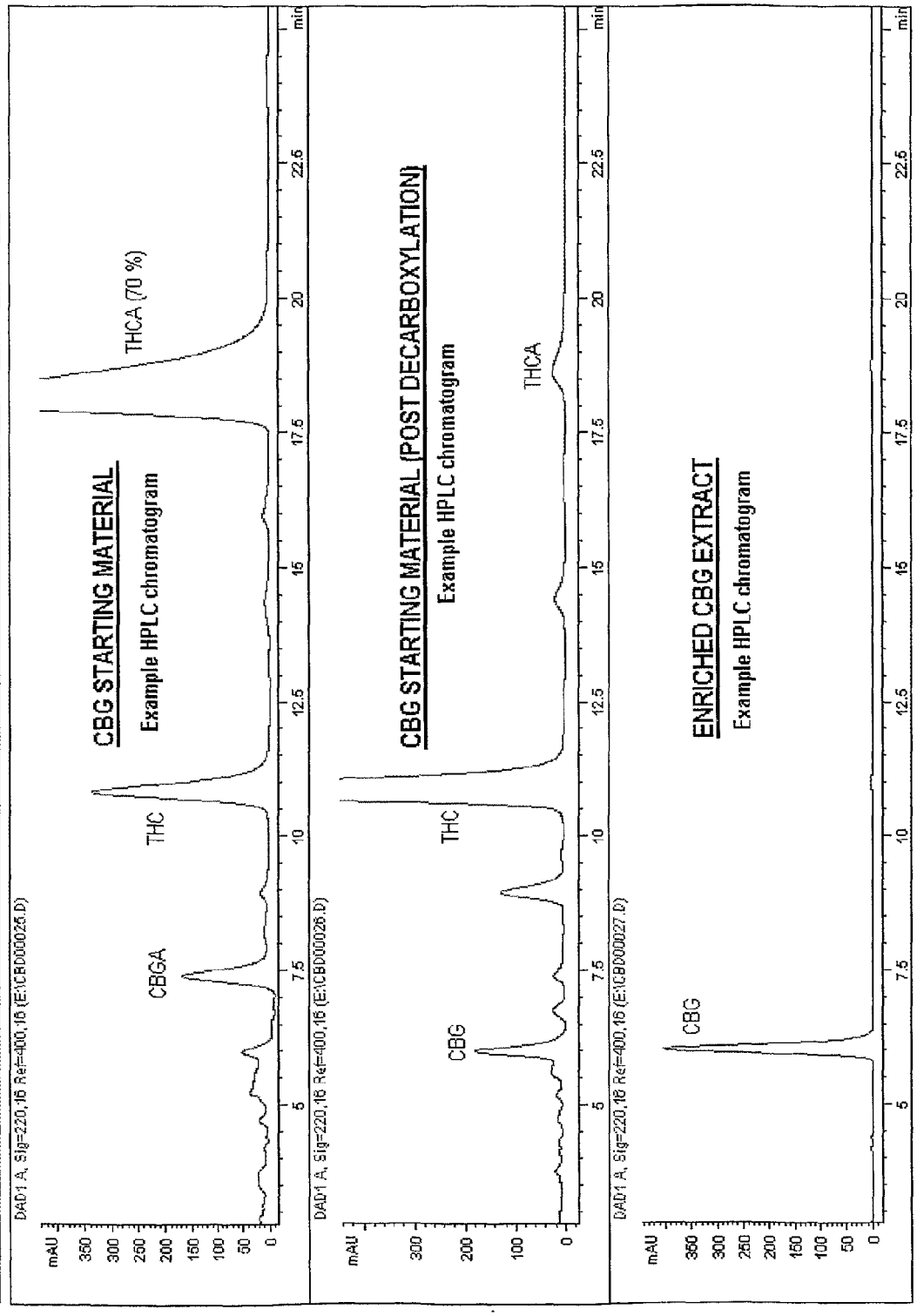
FIGURE 14: HPLC profiles of G41 chemovar starting material, pre and post decarboxylation, and enriched CBG extract

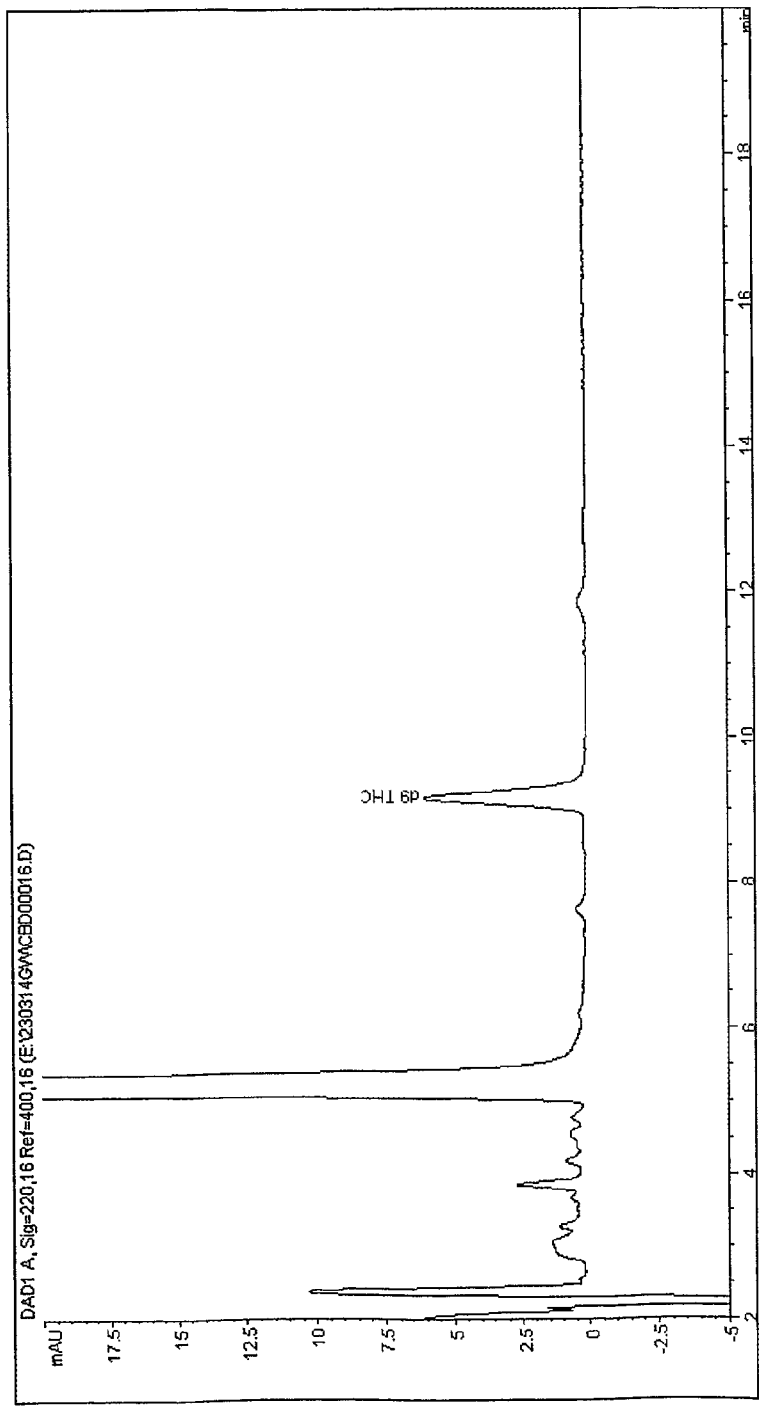
Figure 15 - HPLC profile of colourless solution CBG preparation

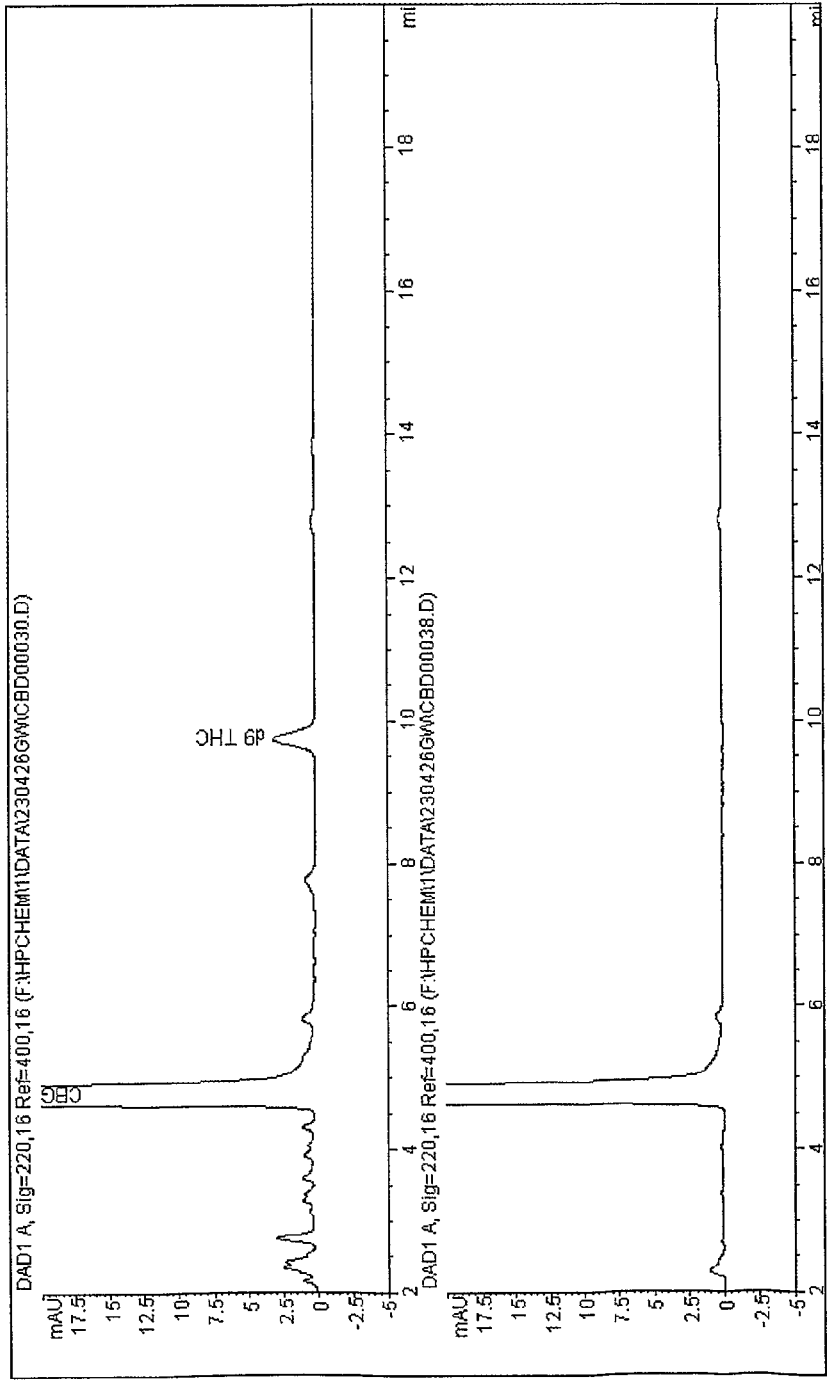
Figure 16 - HPLC profile of further flash chromatography purified CBG preparation compared to improved purity CBG

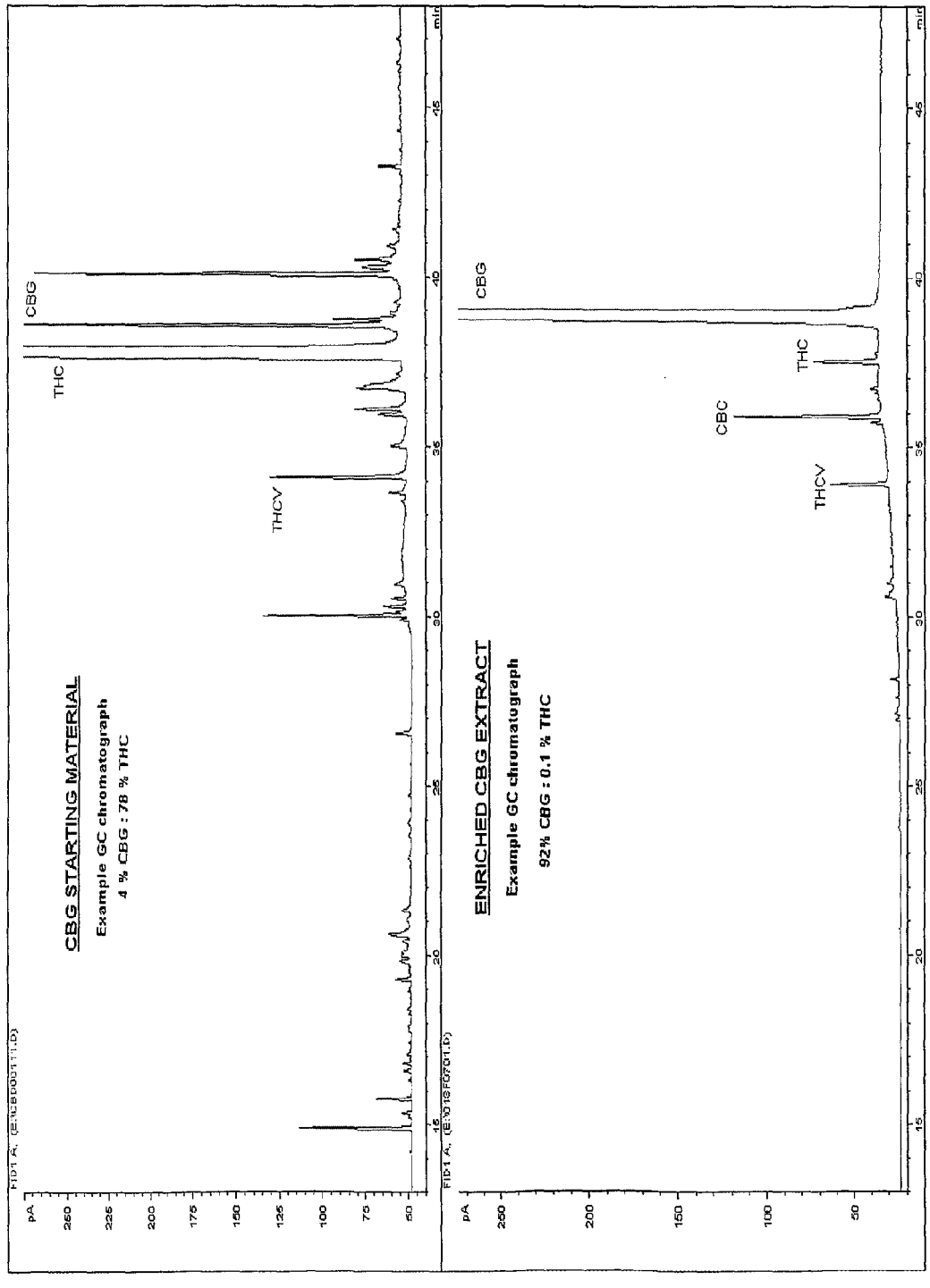
FIGURE 17: GC profiles of G41 chemovar starting material (post decarboxylation) and enriched CBG extract.

Figure 18: TLC profiles of G80 chemovar starting material (post decarboxylation) and enriched CBC extract.
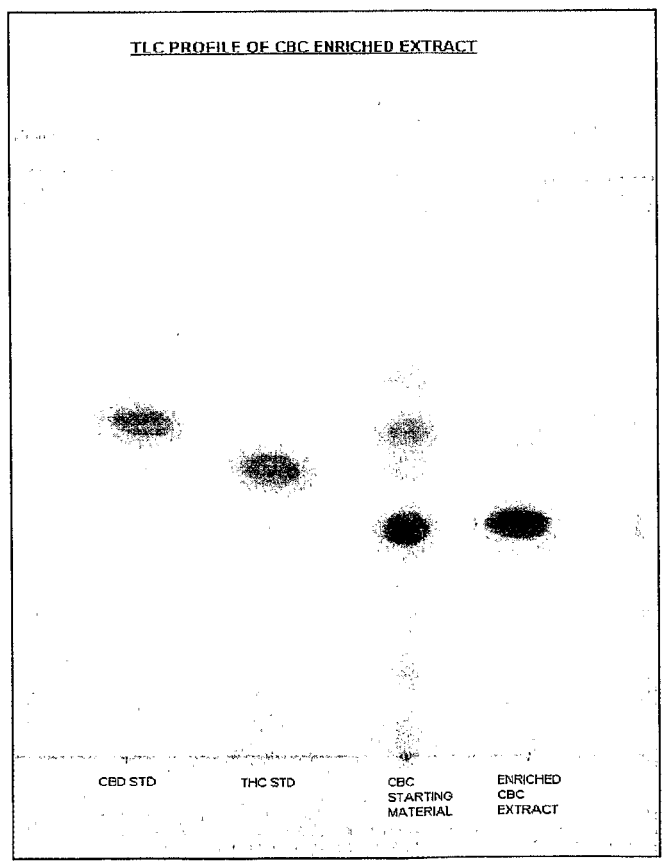

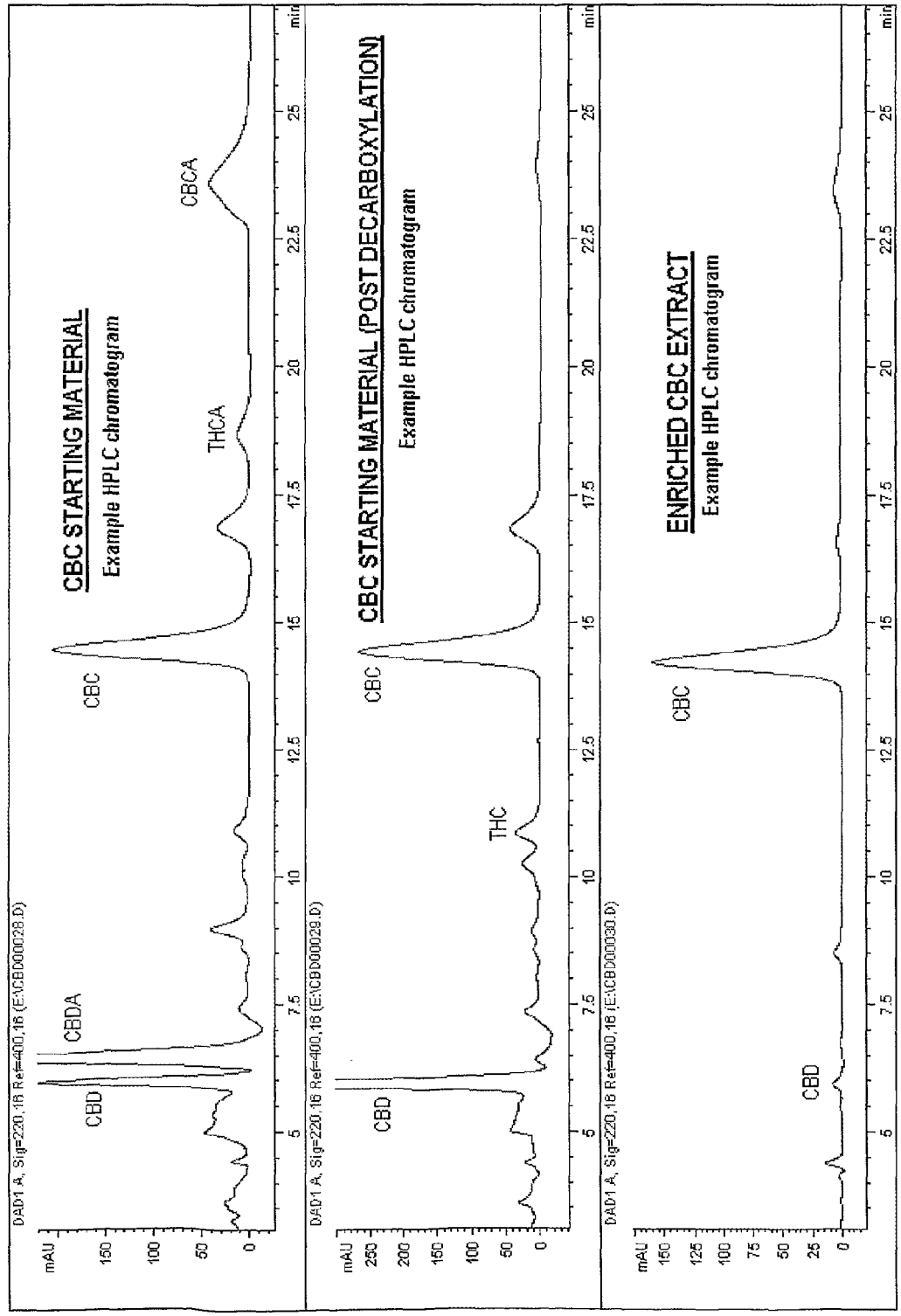
FIGURE 19: HPLC profiles of G80 chemovar starting material, pre and post decarboxylation, and enriched CBC extract.

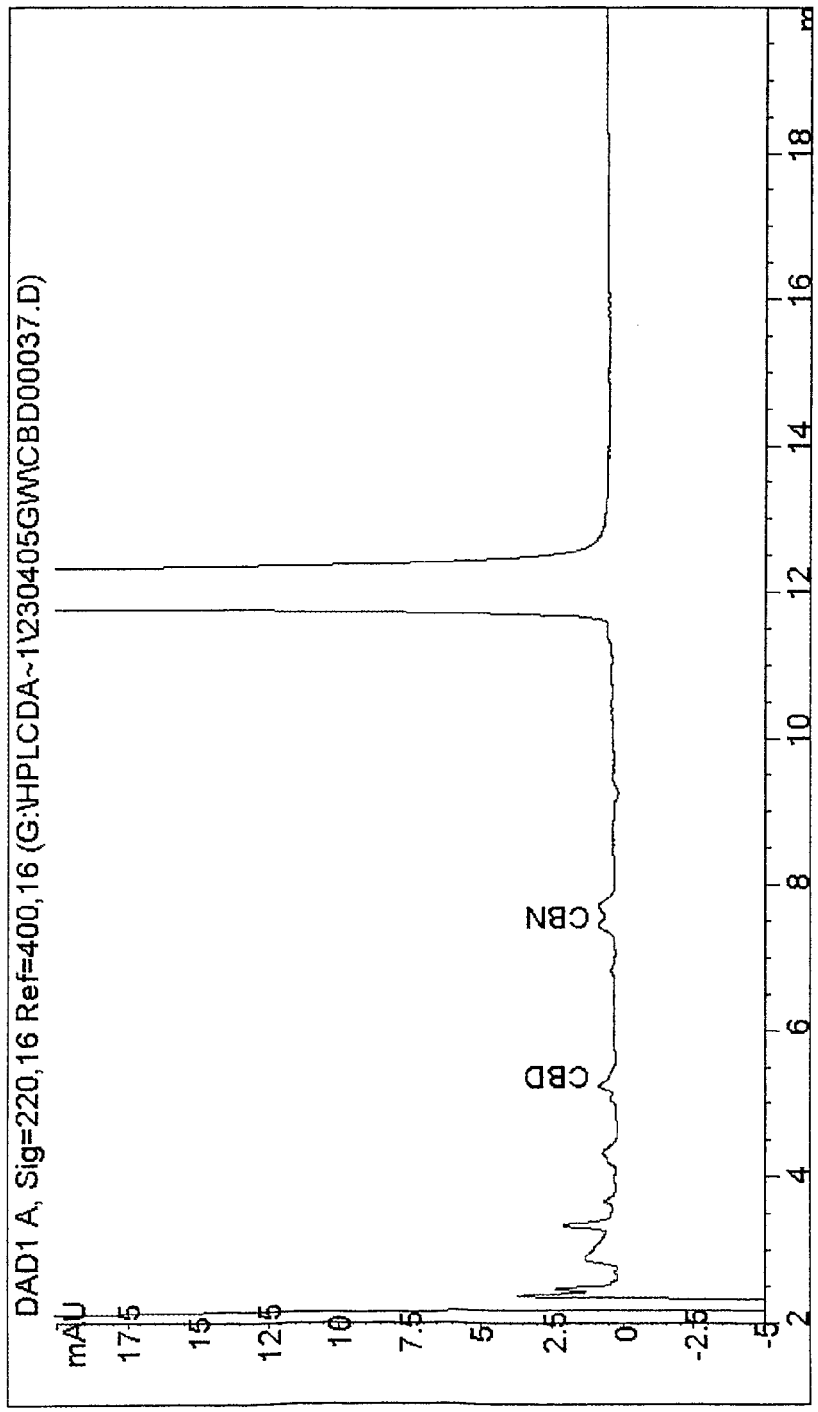

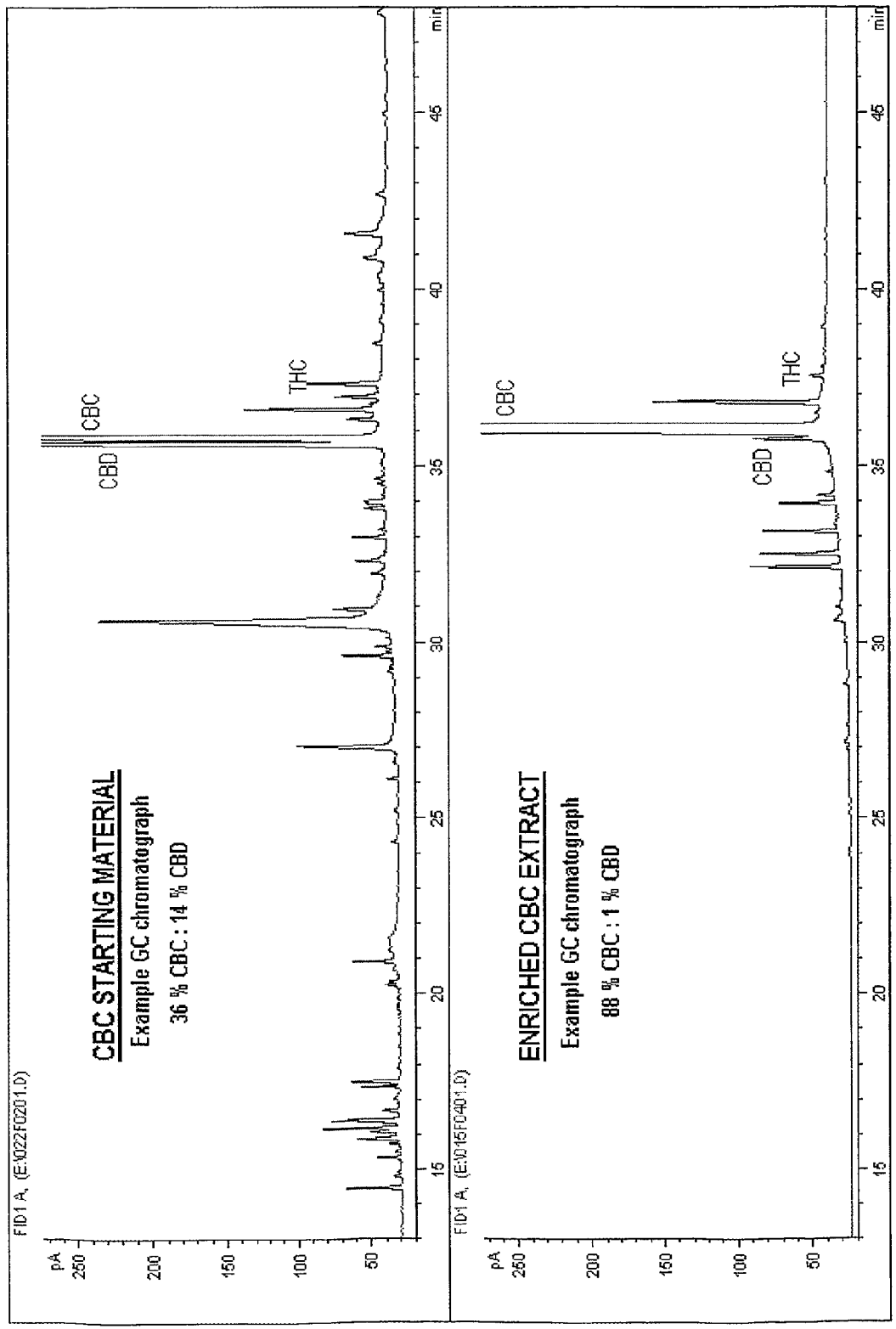
FIGURE 21: GC profiles of G80 chemovar starting material (post decarboxylation) and enriched CBC extract.

US 8,846,409 B2

METHODS OF PREPARING CANNABINOIDS FROM PLANT MATERIAL

RELATED APPLICATIONS

This application is a continuation application of U.S. patent application Ser. No. 10/528,951, filed Mar. 22, 2005, now allowed, which is a national stage filing under 35 U.S.C. §371 of PCT International application PCT/GB03/04078, filed Sep. 23, 2003, which was published under PCT Article 21(2) in English, the contents of each of which are incorporated by reference herein.

FIELD OF THE INVENTION

The invention relates to methods of preparing cannabinoids in substantially pure form starting from plant material.

BACKGROUND TO THE INVENTION

*Cannabis* has been used medicinally for many years, and in Victorian times was a widely used component of prescription medicines. It was used as a hypnotic sedative for the treatment of "hysteria, delirium, epilepsy, nervous insomnia, migraine, pain and dysmenorrhoea". Historically, *cannabis* was regarded by many physicians as unique; having the ability to counteract pain resistant to opioid analgesics, in conditions such as spinal cord injury, and other forms of neuropathic pain including pain and spasm in multiple sclerosis.

The use of *cannabis* continued until the middle of the twentieth century, when the recreational use of *cannabis* prompted legislation which resulted in the prohibition of its use. The utility of *cannabis* as a prescription medicine is now being re-evaluated. The discovery of specific cannabinoid receptors and new methods of administration have made it possible to extend the use of *cannabis*-based medicines to historic and novel indications.

The principle cannabinoid components present in herbal *cannabis* are the cannabinoid acids $\Delta^9$ tetrahydrocannabinolic acid ($\Delta^9$ THCA) and cannabidiolic acid (CBDA), with small amounts of the corresponding neutral cannabinoids, respectively $\Delta^9$ tetrahydrocannabinol ($\Delta^9$ THC) and cannabidiol (CBD). Cannabidiol was formerly regarded as an inactive constituent, however there is emerging evidence that it has pharmacological activity, which is different from that of $\Delta^9$ THC in several respects.

In addition to these major cannabinoids, herbal *cannabis* may contain lower levels of other minor cannabinoids. These may be intermediates in the biosynthesis of the major cannabinoids and hence exist at only low levels in the plant as they are constantly undergoing further biotransformation once they are formed. An example of such a cannabinoid is cannabigerol (CBG). Other minor cannabinoids may represent the end point of an alternative biosynthetic pathway to that leading to the formation of the major cannabinoids $\Delta^9$ THC and CBD. These cannabinoids are frequently relatively more abundant in the plant, an example being cannabichromene (CBC).

A special example of a minor cannabinoid that is the end point of a biosynthetic pathway is $\Delta^9$ Tetrahydrocannabivarin ($\Delta^9$ THCV). This compound is closely related to $\Delta^9$ THC, with the only difference in structure being the presence of a propyl ($C_3H_7$) side chain rather than a pentyl ($C_5H_{11}$) side chain on the aromatic ring. This compound usually accompanies $\Delta^9$ THC at a level of 1-2% of THC present. However in certain selectively bred varieties of *cannabis* $\Delta^9$ THCV can account for greater than 70% of total cannabinoids, with $\Delta^9$ THC being reduced to the level of a minor constituent.

Purified forms of certain of the cannabinoids present in herbal *cannabis* are useful as active pharmaceutical agents. For example, $\Delta^9$ THC (also known as dronabinol) has been approved by the Food and Drug Administration (FDA) for the control of nausea and vomiting associated with chemotherapy, and also shows potential pharmacological activity in the treatment of glaucoma, migraine headaches, anxiety, and as an analgesic. Cannabidiol, formerly regarded as an inactive constituent of *cannabis*, has, as aforesaid, itself shown promising pharmacological activity.

In the case of the minor cannabinoids, the difficulties in isolating the minor cannabinoids in a pure state and the absence of commercially available standards have restricted the investigation of the pharmacology of these compounds and their true therapeutic potential is unknown. Consequently it is of great interest to isolate sufficiently pure samples of these cannabinoids in the quantities required to permit pharmacological studies to be performed.

Purified forms of the cannabinoids and cannabinoid acids are also potentially useful as analytical standards, particularly in the characterisation of *cannabis*-derived medicines based on botanical drug substances prepared from herbal *cannabis*.

Thus, there remains a need for purified forms of all of the cannabinoid acids and cannabinoids present in *cannabis* herb, including the major cannabinoids $\Delta^9$ THC and CBD and the minor cannabinoids.

Synthetic forms of certain of the cannabinoids, particularly $\Delta^9$ THC, CBD and CBN, are commercially available. However, synthetic cannabinoids are extremely expensive. Attention has therefore focussed on the purification of cannabinoids from plant material.

WO 02/32420 discloses a process for preparing, for example, $\Delta^9$-THC from plant material. It utilises $CO_2$ extraction and ethanol precipitation to obtain "primary extracts" containing $\Delta^9$-THC and CBD, with reduced amounts of, for example, monoterpenes, sesquiterpenes, hydrocarbons, alkaloids, flavonoids and chlorophylls. The CBD is then converted to $\Delta^9$-THC by a catalysing reaction. The cannabinoids make up only approximately two-thirds of the composition and are therefore not substantially pure.

U.S. Pat. No. 6,403,126 discloses a process in which THC is removed from a *cannabis* extract using chromatography.

JP 3153625 discloses a method of producing an anti-allergic agent. In one example, dry seeds of *cannabis* are subjected to multiple extraction steps and multiple chromatographic steps.

Biochemical Medicine (1973, vol. 8, P. 341-344) discloses a multi-step extraction and purification process for producing $\Delta^9$-THC of unspecified purity.

ODCCP Bulletin on Narcotics (1976, Issue 4) discloses a method of isolating CBD, THC and CBN using preparative gas chromatography.

U.S. Pat. No. 6,365,416 describes a method of preparing $\Delta^9$ THC from plant material which involves extracting the plant material with a non-polar organic solvent, optionally subjecting the extract to a column chromatography step to produce a residue eluate, subjecting the extract or the residue eluate to a low pressure flash distillation to produce a distillate, optionally subjecting the distillate to a second flash distillation step, and subjecting the distillate to column chromotography, normal HPLC or reverse-phase HPLC. The process provides a product containing $\Delta^9$ THC in an amount greater than 90% by weight.

There remains a need for alternative purification processes which may be used to prepare purified forms of all cannabinoid and cannabinoid acid constituents of *cannabis* herb, including the cannabinoid acids $\Delta^9$ THCA and CBDA, the corresponding free cannabinoids $\Delta^9$ THC and CBD, and the minor cannabinoids. The present invention relates to such a purification process based on a simple combination of solvent extraction, chromatography and re-crystallisation steps. The process is simple, efficient and economic, and is capable of producing cannabinoids of high purity, whilst avoiding the need for preparatory HPLC.

SUMMARY OF THE INVENTION

In a first aspect the invention provides a method of obtaining a substantially pure cannabinoid or cannabinoid acid or a product enriched in a given cannabinoid or cannabinoid acid comprising:

i) obtaining an extract containing a cannabinoid or cannabinoid acid from a plant material;
ii) subjecting the extract of step (i) to a chromatographic step to produce a partially purified extract;
iii) dissolving the partially purified extract in a first solvent, removing any insoluble material therefrom, and removing the solvent; and
iv) dissolving the product obtained in step iii) in a second solvent, removing any insoluble material therefrom, and removing the solvent to obtain the substantially pure cannabinoid or cannabinoid acid or the product enriched in a given cannabinoid or cannabinoid acid, wherein the first and second solvents are different, and wherein one of the first or second solvents is a solvent which is substantially more polar than the cannabinoid/cannabinoid acid which it is desired to purify, and the other solvent is a solvent which is substantially less polar than the cannabinoid/cannabinoid acid which it is desired to purify.

The method may optionally comprise a further step v) of flash chromatography as an optional further purification step. In the most preferred embodiment the flash chromatography step may comprise the following:

v) loading the substantially pure cannabinoid or cannabinoid acid or the product enriched in a given cannabinoid or cannabinoid acid onto a Chromabond Flash BT 12M silica cartridge column, eluting with hexane:ethyl acetate (98:2) at a flow rate of approximately 5 ml/min.

The invention further relates to substantially pure preparations of various cannabinoids and cannabinoid acids and also products enriched in various cannabinoids and cannabinoid acids.

DESCRIPTION OF THE INVENTION

The invention relates to a purification process for preparing substantially pure cannabinoid or cannabinoid acid or a product enriched in a given cannabinoid or cannabinoid acid from plant material.

A "substantially pure" preparation of cannabinoid or cannabinoid acid is defined as a preparation having a chromatographic purity (of the desired cannabinoid or cannabinoid acid) of greater than 95%, more preferably greater than 96%, more preferably greater than 97%, more preferably greater than 98%, more preferably greater than 99% and most preferably greater than 99.5%, as determined by area normalisation of an HPLC profile.

The term "product enriched in a given cannabinoid or cannabinoid acid" encompasses preparations having at least 80%, preferable greater than 85%, more preferably greater than 90% chromatographic purity for the desired cannabinoid or cannabinoid acid. Such a product will generally contain a greater proportion of impurities, non-target materials and other cannabinoids than a "substantially pure" preparation.

The method of the invention may be used to extract/purify cannabinoids or cannabinoid acids from any plant material known to contain such cannabinoids or cannabinoid acids. Most typically, but not necessarily, the "plant material" will be derived from one or more *cannabis* plants.

The term "plant material" encompasses a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Centre for Drug Evaluation and Research.

The term "*cannabis* plant(s)" encompasses wild type *Cannabis sativa* and also variants thereof, including *cannabis* chemovars (varieties characterised by virtue of chemical composition) which naturally contain different amounts of the individual cannabinoids, also *Cannabis sativa* subspecies *indica* including the variants var. *indica* and var. *kafiristanica*, *Cannabis indica* and also plants which are the result of genetic crosses, self-crosses or hybrids thereof. The term "*cannabis* plant material" is to be interpreted accordingly as encompassing plant material derived from one or more *cannabis* plants. For the avoidance of doubt it is hereby stated that "*cannabis* plant material" includes herbal *cannabis* and dried *cannabis* biomass.

"Decarboxylated *cannabis* plant material" refers to *cannabis* plant material which has been subject to a decarboxylation step in order to convert cannabinoid acids to the corresponding free cannabinoids.

The starting material for the purification process is an extract containing a cannabinoid or cannabinoid acid obtained from a plant material.

In a preferred embodiment the "extract containing a cannabinoid or cannabinoid acid" may be a solvent extract of a plant material. Preferred extraction solvents for use in the preparation of this extract include non-polar solvents, also alcohols such as ethanol or methanol and liquid carbon dioxide. Preferably the extract is prepared by dissolving plant material in an extraction solvent, removing insoluble material from the resultant solution (preferably by filtration), and removing the extraction solvent from the solution (preferably by rotary evaporation) to form an extract containing a cannabinoid or cannabinoid acid.

Non-polar solvents are particularly preferred for preparing an initial extract from the starting plant material. Any non-polar solvent capable of solubilising cannabinoids or cannabinoid acids may be used. Preferred non-polar solvents include liquid non-polar solvents comprising lower C5-C12, preferably C5 to C8, straight chain or branched chain alkanes. The most preferred non-polar solvent for the preparation of free cannabinoids is hexane.

In embodiments wherein the method is to be used for the isolation of cannabinoid acids then it is preferred to use an acidified extraction solvent to prepare the initial extract. The primary purpose of this acidification is to prevent/minimise ionisation of the cannabinoid acid, which could otherwise adversely affect the purification process. It is preferred to use acidified non-polar solvents, of the types described above. Acidification may be achieved by the additional of a small volume of acid to the solvent. Generally it is sufficient to add a relatively weak acid, such as acetic acid. For any given purification process the optimal amount and type of acid used may be determined empirically. A preferred acidified solvent is 0.1% acetic acid in hexane. This is the extraction solvent of choice for preparing an initial extract from the starting plant material in the preparation of cannabinoid acids.

In embodiments of the method where it is desired to purify free cannabinoids, rather than the cannabinoid acids, the plant material may be subjected to a decarboxylation step prior to step (i). The purpose of the decarboxylation step is to convert cannabinoid acids present in the plant material to the corresponding free cannabinoids. Decarboxylation is preferably carried out by heating the plant material to a defined temperature for a suitable length of time. Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimising thermal degradation of the desirable, pharmacological cannabinoids into undesirable degradation products, particularly thermal degradation of $\Delta^9$ THC to cannabinol (CBN).

Preferably, decarboxylation is carried out in a multi-step heating process in which the plant material is:

i) heated to a first temperature for a first (relatively short) time period to evaporate off retained water and allow for uniform heating of the plant material; and ii) the temperature is increased to a second temperature for a second time period (typically longer than the first time period) until at least 95% conversion of the acid cannabinoids to their neutral form has occurred.

Preferably the first step is conducted at a temperature in the range of from 100° C. to 110° C. for 10-20 min. More preferably the first temperature is about 105° C. and the first time period is about 15 minutes.

Optimum times and temperatures for the second step may vary depending on the nature of the plant material, and more particularly on the cannabinoid which it is intended to isolate from the plant material, and may be easily determined by routine experiment. Suitable conditions may include, for example, a temperature in the range of from 115° C. to 125° C. for a time period in the range of from 45 to 75 minutes (typically 120° C. for 60 minutes), or a temperature in the range of from 135° C. to 145° C., for a time period in the range of from 15 to 45 minutes.

If the plant material is derived from *cannabis* plants having a high THC content (defined as >90% THC as a percentage of total cannabinoid content), the second temperature is preferably in the range of from 115° C. to 125° C., typically 120° C., and the second time period is preferably in the range of from 45 minutes to 75 minutes, typically about 60 minutes. More preferably the second temperature is in the range of from 100° C. to 110° C., typically 105° C., and the second time period is in the range of from 60 to 120 minutes. In another embodiment, most preferred for a mass of plant material greater than 4 kg, the second temperature is in the range of from 140° C. to 150° C., preferably 145° C., and the second time period is in the range of from 45 to 55 minutes.

Where the starting "plant material" is freshly harvested or "wet" plant material is may be subjected to a drying step to remove excess moisture prior to step (i). For convenience, decarboxylation and drying may be combined in a single heating step or in a multi-step heating process, as described above.

In a particular embodiment of the method of the invention the "extract containing a cannabinoid or cannabinoid acid" prepared from the starting plant material may be a "botanical drug substance" prepared from the plant material, or an ethanolic solution of such a botanical drug substance. In the context of this application a "botanical drug substance" is an extract derived from plant material, which extract fulfils the definition of "botanical drug substance" provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverisation, decoction, expression, aqueous extraction, ethanolic extraction, or other similar processes."

"Botanical drug substances" derived from *cannabis* plants include primary extracts prepared by such processes as, for example, maceration, percolation, and solvent extraction. Solvent extraction may be carried out using essentially any solvent that dissolves cannabinoids/cannabinoid acids, such as for example C1 to C5 alcohols (e.g. ethanol, methanol), C5-C12 alkanes (e.g. hexane), Norflurane (HFA134a), HFA227 and carbon dioxide. When solvents such as those listed above are used, the resultant extract typically contains non-specific lipid-soluble material. This can be removed by a variety of processes including "winterisation", which involves chilling to −20° C. followed by filtration to remove waxy ballast, extraction with liquid carbon dioxide and by distillation. General protocols for the preparation of botanical drug substances from *cannabis* plant material are described in the applicant's published International patent application WO 02/064109.

The botanical drug substance is preferably obtained by carbon, dioxide ($CO_2$) extraction followed by a secondary extraction, e.g. an ethanolic precipitation, to remove a substantial proportion of non-cannabinoid materials, e.g. waxes, wax esters and glycerides, unsaturated fatty acid residues, terpenes, carotenes, and flavenoids and other ballast. Most preferably the botanical drug substance is produced by a process comprising extraction with liquid $CO_2$, under sub-critical or super-critical conditions, and then a further extraction, preferably an ethanolic precipitation, to remove significant amounts of ballast.

If it is intended to prepare free cannabinoids from the *cannabis* plant material then the material is preferably heated to a defined temperature for a defined period of time in order to decarboxylate cannabinoid acids to free cannabinoids prior to extraction of the botanical drug substance.

In the most preferred embodiment the botanical drug substance is prepared according to a process comprising the following steps:

i) optional decarboxylation of the plant material, ii) extraction with liquid $CO_2$ (most preferably under sub-critical conditions), to produce a crude botanical drug substance, iii) precipitation with C1-C5 alcohol to reduce the proportion of non-target materials, iv) removal of the precipitate (preferably by filtration), v) optional treatment with activated charcoal, and vi) evaporation to remove C1-C5 alcohol and water, thereby producing a final botanical drug substance.

A detailed example of such a process is described in the accompanying Examples.

The "extract containing a cannabinoid or cannabinoid acid" is subjected to a chromatographic purification step to produce a partially purified extract. The purpose of this step is to reduce the amount of "non-target", i.e. non-cannabinoid or non-cannabinoid acid material, in the extract and also to provide a degree of separation/fractionation of the various cannabinoid/cannabinoid acid components of the crude plant extract obtained in step (i). Typically, the product of the chromatographic step is collected in multiple fractions, which may then be tested for the presence of the desired cannabinoid/cannabinoid acid using any suitable analytical technique (e.g. TLC). Fractions enriched in the desired cannabinoid/cannabinoid acid may then be selected for further purification.

The chromatographic step will preferably comprise column chromatography, and is preferably based on molecular sizing and polarity. Preferred column matrix materials are hydrophilic lipophilic materials, for example hydroxypropylated cross-linked dextrans such as Sephadex LH-20™. Various different solvents may be used in combination with this type of matrix, for example dimethyl sulphoxide, pyridine, water, dimethylformamide, methanol, saline, ethylene dichloride, chloroform, propanol, ethanol, isobutanol, formamide, methylene dichloride, butanol, isopropanol, tetrahydrofuran, dioxane, chloroform/dichloromethane etc.

In the most preferred embodiment the chromatographic step comprises column chromatography on a Sephadex LH-20™ column, preferably eluting with a 2:1 mixture of chloroform/dichloromethane. However, any suitable combination of column packing material and solvent having separation characteristics suitable for use in separation (fractionation) of cannabinoids and cannabinoid acids may be used with equivalent effect. The column eluate is typically collected in several fractions. The fractions are tested for the presence of the desired cannabinoid/cannabinoid acid using a suitable analytical technique, and those fractions containing the highest amounts of the desired cannabinoid or cannabinoid acid selected for further processing. Solvent is then removed from the selected fractions, preferably by rotary evaporation.

The partially purified product obtained from the chromatographic step is re-dissolved in a first solvent. Any insoluble residues (e.g. particulate material) are removed from the resultant solution, typically by filtration. The first solvent is then removed, preferably by rotary evaporation. The product of this step is re-dissolved in a second solvent. Again, any insoluble residues (e.g. particulate material) are removed from the resultant solution, typically by filtration. The second solvent is then removed, preferably by rotary evaporation, to produce the final product, which is a substantial pure cannabinoid or cannabinoid acid or a product enriched in a given cannabinoid or cannabinoid acid.

The purpose of these two "solvent treatment" steps is to remove contaminants, leaving a substantially pure preparation of the desired cannabinoid or cannabinoid acid.

In the preferred embodiment the first and second solvents are different. One of the first or second solvents is a solvent which is substantially more polar than the cannabinoid/cannabinoid acid which it is desired to purify. Treatment with this solvent has the effect of removing unwanted components that are less polar than the desired cannabinoid/cannabinoid acid. The other solvent is a solvent which is substantially less polar than the cannabinoid/cannabinoid acid which it is desired to purify. Treatment with this solvent has the effect of removing unwanted components that are more polar than the desired cannabinoid/cannabinoid acid. The combined effect of sequential treatment with two such solvents is of "topping and tailing" the partially purified extract to yield a substantially pure product. The two solvent treatment steps may be performed in either order. It is immaterial to the overall purification whether the "less polar" or "more polar" contaminants are removed first.

The first and second solvents may be essentially any solvents that dissolve cannabinoids and/or cannabinoid acids and which have the desired polarity in comparison to the cannabinoid/cannabinoid acid which it is desired to isolate.

Preferred solvents for use in these treatment steps include alcohols, particularly C1-C5 alcohols, with methanol being particularly preferred, and also C5-C12 straight or branched chain alkanes, most preferably pentane. A particularly preferred combination of first and second solvents, which is suitable for use in the preparation of the majority of cannabinoids and cannabinoid acids, is methanol and pentane. These solvents may be used in either order.

The process of the invention generally results in the isolation of substantially pure cannabinoids or cannabinoid acids of high chromatographic purity. Substantially pure cannabinoids or cannabinoid acids are often obtained as crystalline solids or clear colourless solutions. The inventors have determined that the process of the invention may be used to prepare substantially pure preparations of cannabinoids or cannabinoid acids having a higher degree of chromatographic purity than the preparations previously known in the prior art. Therefore, in an extremely important aspect, the process of the invention provides a solution to the problem of preparing/isolating cannabinoids and cannabinoid acids at a high degree of purity. The process is advantageously cheap, amenable to scale-up and applicable to a wide range of different cannabinoids and cannabinoid acids.

The process of the invention may be used to prepare substantially pure forms, or products enriched in, essentially any cannabinoids or cannabinoid acids which occur naturally in plant material (including free cannabinoid forms of naturally occurring cannabinoid acids).

The essential features of the process are the same for purification of all cannabinoids and cannabinoid acids. *Cannabis* plants generally contain complex mixtures of cannabinoid acids and cannabinoids, although depending on the variety of *cannabis* one type of cannabinoid may pre-dominate. The purpose of the chromatographic step (ii) is to separate the various cannabinoid/cannabinoid acid components of the crude plant extract obtained in step (i). Typically, the product of the chromatographic step is collected in multiple fractions, which may then be tested for the presence of the desired cannabinoid/cannabinoid acid using any suitable analytical technique (e.g. TLC). Fractions enriched in the desired cannabinoid/cannabinoid acid may then be selected for further purification. Hence, the same simple process steps may be adapted for purification of essentially any plant-derived cannabinoid or cannabinoid acid.

Selectivity for different cannabinoids or cannabinoid acids may be enhanced by selection of appropriate starting plant material. By way of example, if it is desired to prepare substantially pure $\Delta^9$ THC or $\Delta^9$ THCA then "high THC" *cannabis* plants should preferably be selected as the starting material. Whereas, if it is desired to prepare substantially pure CBD or CBDA then "high CBD" *cannabis* plants should preferably be selected as the starting material. However, it is to be understood that the process of the invention is of general utility and is not limited to the use of particular *cannabis* varieties as the starting material.

Working with *Cannabis* plants and cannabinoids may require a Government licence in some territories but Governments generally make such licences available to parties who apply for the purposes of medicinal research and commercial development of medicines. In the United Kingdom a licence may be obtained from the Home Office.

The precise cannabinoid content of any particular *cannabis* plant material may be qualitatively and quantitatively determined using analytical techniques well known to those skilled in the art, such as thin-layer chromatography (TLC) or high performance liquid chromatography (HPLC). Thus, one may screen a range of from *cannabis* plants and select those having a high content of the desired cannabinoid acid or cannabinoid for use as starting material in the process of the invention.

With the use of conventional selective breeding techniques it is possible to develop *cannabis* varieties (chemovars) having varying cannabinoid content. Using such traditional selective breeding techniques the inventors have been able to select *cannabis* varieties (chemovars) having relatively high content of CBD, or of the minor cannabinoids $\Delta^9$ tetrahydrocannabivarin ($\Delta^9$ THCV), cannabigerol (CBG) or cannabichromene (CBC). General protocols for growing of medicinal *cannabis* and for testing the cannabinoid content of *cannabis* plants are described in the applicant's published International patent application WO 02/064109.

Where it is desired to purify free cannabinoids, rather than the corresponding cannabinoid acids, then the process will generally include a "decarboxylation" step to decarboxylate free cannabinoid acids to the corresponding free cannabinoid. As aforesaid, a decarboxylation step may be included prior to step (i) if it is desired to isolate free cannabinoids, or omitted if it is desired to isolate cannabinoid acids.

The process of the invention is particularly preferred for use in the preparation of substantially pure $\Delta^9$ tetrahydrocannabinolic acid ($\Delta^9$ THCA), cannabidiolic acid (CBDA), $\Delta^9$ tetrahydrocannabinol ($\Delta^9$ THC) and $\Delta^9$ tetrahydrocannabivarin ($\Delta^9$ THCV) from *cannabis* plant material, and in the preparation of extracts of *cannabis* plant material highly enriched in cannabigerol (CBG) or cannabichromene (CBC).

The invention further relates to substantially pure preparations of certain cannabinoids and cannabinoids and to products highly enriched in certain cannabinoids.

In particular, the invention provides a substantially pure preparation of $\Delta^9$ tetrahydrocannabinolic acid ($\Delta^9$ THCA) having a chromatographic purity of greater than 95%, more preferably greater than 96%, more preferably greater than 97% and most preferably greater than 98% by area normalisation of an HPLC profile. The preparation is typically a pale yellow crystalline solid at room temperature, having a melting point of −70° C.

The preparation preferably comprises:
less than 2%, preferably less than 1.5%, most preferably 1% or less $\Delta^9$ THC (w/w),
less than 2%, more preferably less than 1.5%, more preferably less than 1% and most preferably less than 0.5% CBD (w/w),
less than 2%, more preferably less than 1.5%, and most preferably less than 1% CBN (w/w).

The inventors are the first to isolate $\Delta^9$ THCA from plant material at this level of purity in crystalline form. Pure $\Delta^9$ THCA is useful as a starting material for the preparation of pure $\Delta^9$ THC by decarboxylation, also as a chromatographic standard.

The preferred method for preparation of substantially pure $\Delta^9$ THCA from *cannabis* plant material comprises:
i) preparing an extract of the *cannabis* plant material with 0.1% v/v acetic acid in hexane,
ii) filtering the resultant extract and removing solvent from filtrate by rotary evaporation to form an extract enriched in $\Delta^9$ THCA,
iii) passing a solution of the resulting $\Delta^9$ THCA enriched extract through a column packed with Sephadex-LH20™, eluting with 2:1 chloroform/dichloromethane,
iv) collecting $\Delta^9$ THCA rich fractions eluted from the column and removing solvent by rotary evaporation,
v) re-dissolving the crude $\Delta^9$ THCA obtained in step iv) in methanol, removing insoluble residue by filtration and removing solvent from filtrate by rotary evaporation,
vi) re-dissolving the product of step v) in pentane, removing insoluble residue by filtration and removing solvent from filtrate by rotary evaporation to produce $\Delta^9$ THCA crystals.

The *cannabis* plant material will preferably be derived from *cannabis* plants having a relatively high $\Delta^9$ THCA content, most preferably *cannabis* plants containing >90% $\Delta^9$ THCA as a percentage of total cannabinoid content.

The invention further provides a substantially pure preparation of cannabidiolic acid (CBDA) having a chromatographic purity of greater than 90%, more preferable greater than 92% and most preferably greater than 94% by area normalisation of an HPLC profile. The preparation is typically a pale yellow crystalline solid at room temperature, having a melting point in the range of from 45-48° C.

The preparation preferably comprises:
5% or less, preferably 4.5% or less, more preferably 4% or less, more preferably 3.5% or less and most preferably 3% or less CBD (w/w),
less than 1%, preferably less than 0.8%, more preferably less than 0.6%, more preferably less than 0.4%, more preferably less than 0.2% and most preferably less than 0.1% $\Delta^9$ THCA (w/w),
less than 1%, preferably less than 0.8%, more preferably less than 0.6%, more preferably less than 0.4%, more preferably less than 0.2% and most preferably less than 0.1% $\Delta^9$ THC (w/w).

Again, the inventors are the first to isolate CBDA from plant material at this level of purity in crystalline form.

The invention further provides a substantially pure preparation of cannabidiolic acid (CBDA) having a chromatographic purity of greater than 94%, more preferably greater than 96% and most preferably greater than 98% by area normalisation of an HPLC profile. The preparation is preferably a clear colourless solution at room temperature.

The preparation typically comprises:
3% or less, more preferably 2% or less, more preferably 1% or less and most preferably 1% or less and most preferably less than 0.1% CBD (w/w),
less than 0.8%, more preferably less than 0.6%, more preferably less than 0.3% THCA (w/w),
less than 1%, preferably less than 0.8%, more preferably less than 0.6%, more preferably less than 0.4%, more preferably less than 0.2% and most preferably less than 0.1% $\Delta^9$-THC (w/w).

Pure CBDA is useful as a starting material for the preparation of pure CBD by decarboxylation, also as a chromatographic standard and may also have pharmaceutical potential. The ability to prepare CBDA at a high level of purity will permit further studies of the pharmaceutical utility of this cannabinoid acid.

The preferred method for preparation of substantially pure CBDA from *cannabis* plant material comprises:
i) preparing an extract of the *cannabis* plant material with 0.1% v/v acetic acid in hexane,
ii) filtering the resultant extract and removing solvent from filtrate by rotary evaporation to form an extract enriched in CBDA,
iii) passing a solution of the resulting CBDA enriched extract through a column packed with Sephadex-LH20™, eluting with 2:1 chloroform/dichloromethane,
iv) collecting CBDA rich fractions eluted from the column and removing solvent by rotary evaporation,
v) re-dissolving the crude CBDA obtained in step iv) in methanol, removing insoluble residue by filtration and removing solvent from filtrate by rotary evaporation, vi) re-dissolving the product of step v) in pentane, removing insoluble residue by filtration and removing solvent from filtrate by rotary evaporation to produce CBDA crystals or a solution.

The *cannabis* plant material will preferably be derived from *cannabis* plants having a relatively high CBDA content, most preferably *cannabis* plants containing >90% CBDA as a percentage of total cannabinoid content.

Where the product of the method is a CBDA solution, the method may optionally include a further purification step of flash chromatography, comprising The method may optionally include a further purification step of flash chromatography comprising vii) loading the substantially pure solution of CBDA onto a Chromabond Flash BT 12M silica cartridge column, eluting with hexane:ethyl acetate (98:2) at a flow rate of approximately 5 ml/min.

The invention further provides a substantially pure preparation of $\Delta^9$ tetrahydrocannabinol ($\Delta^9$ THC) having a chromatographic purity of greater than 99% by area normalisation of an HPLC profile. The preparation is a semi-solid at room temperature.

The preparation preferably comprises less 0.5%, preferably than 0.4%, more preferably less than 0.2% and most preferably less than 0.1% CBD (w/w),
less than 0.5%, preferably less than 0.4%, more preferably less than 0.2% and most preferably less than 0.1% CBN (w/w).

Most preferably the preparation contains no detectable (<0.1%) CBD and no detectable CBN (<0.1%), as analysed by HPLC.

The inventors are the first to isolate $\Delta^9$ THC from plant material at >99% purity and in semi-solid form. $\Delta^9$ THC has previously been reported in the literature as a yellow oil and has never been obtained in crystalline form. The pure $\Delta^9$ THC is of obvious utility as an active pharmaceutical agent, and is also useful as a chromatographic standard, particularly as a comparative standard in the qualitative analysis of botanical drug substances derived from *cannabis*. The availability of highly pure $\Delta^9$ THC will also facilitate studies of the pharmacology of $\Delta^9$ THC.

The preferred method for preparation of substantially pure $\Delta^9$ THC comprises:
i) obtaining an ethanolic solution of a botanical drug substance from decarboxylated *cannabis* plant material,
ii) passing the solution obtained in step i) through a column of activated charcoal, and collecting the eluate,
iii) remove solvent from the eluate by rotary evaporation to give a $\Delta^9$ THC enriched fraction,
iv) passing a solution of the resulting $\Delta^9$ THC enriched extract through a column packed with Sephadex LH20, eluting with 2:1 chloroform/dichloromethane,
v) collecting $\Delta^9$ THC rich fractions and removing solvent by rotary evaporation,
vi) re-dissolving the crude $\Delta^9$ THC prepared in step v) in methanol, removing insoluble residue by filtration and removing solvent from filtrate by rotary evaporation,
vii) re-dissolving the crude $\Delta^9$ THC prepared in step vi) in pentane, removing insoluble residue by filtration and removing solvent from the filtrate by rotary evaporation to give a semi-solid preparation of $\Delta^9$ THC.

In this method the ethanolic solution of a botanical drug substance from decarboxylated *cannabis* plant material is preferably obtained by a method comprising the following steps:
i) harvesting *cannabis* plant material,
ii) decarboxylation of the plant material,
iii) extraction with liquid carbon dioxide ($CO_2$), removal of $CO_2$ to recover crude extract,
iv) dissolution of crude extract in ethanol followed by chilling of the solution to precipitate unwanted waxes,
v) removal of unwanted waxy material by cold filtration.

The (decarboxylated) *cannabis* plant material will preferably be derived from *cannabis* plants having a relatively high THC content, most preferably *cannabis* plants containing >90% THC ($\Delta^9$ THCA plus $\Delta^9$ THC) as a percentage of total cannabinoid content. The plant material is subject to decarboxylation in order to convert the naturally occurring $\Delta^9$ THCA into $\Delta^9$ THC.

The invention still further relates to a substantially pure preparation of $\Delta^9$ tetrahydrocannabivarin ($\Delta^9$ THCV) having a chromatographic purity of greater than 95%, more preferable greater than 96%, more preferable greater than 97%, more preferable greater than 98%, and most preferable greater than 99% by area normalisation of an HPLC profile. The preparation is typically a crystalline solid at room temperature.

The preparation preferably comprises less than 1%, preferably less than 0.8%, more preferably less than 0.6%, more preferably less than 0.4%, more preferably less than 0.2% and most preferably less than 0.1% CBD (w/w),
less than 2.0%, preferably less than 1.5%, more preferably less than 1.0% and most preferably 0.5% or less $\Delta^9$ THC (w/w),
less than 1%, preferably less than 0.8%, more preferably less than 0.6%, more preferably less than 0.4%, more preferably less than 0.2% and most preferably less than 0.1% CBN (w/w).

Again the inventors are the first to isolate $\Delta^9$ THCV from plant material at this level of purity and in crystalline form. The availability of pure $\Delta^9$ THCV will permit studies of the pharmacology of this minor cannabinoid and evaluation of its pharmaceutical potential. Pure $\Delta^9$ THCV is also useful as a chromatographic standard and as a starting material for the preparation of pure cannabivarin (CBV), for example by thermal degradation of $\Delta^9$ THCV in air.

The preferred method for preparation of substantially pure $\Delta^9$ THCV from plant material comprises:
i) obtaining an ethanolic solution of a botanical drug substance from *cannabis* plant material,
ii) passing the solution obtained in step i) through a column of activated charcoal, and collecting the eluate,
iii) remove solvent from the eluate by rotary evaporation to give a $\Delta^9$ THCV enriched fraction,
iv) passing a solution of the resulting $\Delta^9$ THCV enriched extract through a column packed with Sephadex LH20, eluting with 2:1 chloroform/dichloromethane,
v) collecting $\Delta^9$ THCV rich fractions and removing solvent by rotary evaporation,
vi) re-dissolving the crude $\Delta^9$ THCV prepared in step v) in methanol, removing insoluble residue by filtration and removing solvent from filtrate by rotary evaporation,
vii) re-dissolving the crude $\Delta^9$ THCV prepared in step vi) in pentane, removing insoluble residue by filtration and removing solvent from the filtrate by rotary evaporation to give crystals of $\Delta^9$ THCV.

The ethanolic solution of a botanical drug substance from *cannabis* plant material is preferably obtained by a method comprising the following steps:
i) harvesting and decarboxylating *cannabis* plant material,
ii) extraction with liquid carbon dioxide ($CO_2$), removal of $CO_2$ to recover crude extract,
iii) dissolution of crude extract in ethanol followed by chilling of the solution to precipitate unwanted waxes, iv) removal of unwanted waxy material by cold filtration.

The *cannabis* plant material will preferably be derived from *cannabis* plants having a relatively high $\Delta^9$ THCV content.

The invention still further comprises a product enriched in cannabigerol (CBG) having a chromatographic purity of greater than 90%, preferably greater than 92% by area normalisation of an HPLC profile.

The product preferably comprises less than 1%, preferably less than 0.8%, more preferably less than 0.6%, more preferably less than 0.4%, more preferably less than 0.2% and most preferably less than 0.1% CBD (w/w)
less than 1%, preferably less than 0.8%, more preferably less than 0.6%, more preferably less than 0.4%, more preferably less than 0.2% and most preferably 0.1% or less $\Delta^9$ THC (w/w).

The product most preferably contains no detectable (<0.1%) CBN or CBD and no more than 0.1% $\Delta^9$ THC, as analysed by HPLC.

Again, the inventors are the first to prepare *cannabis* plant extracts containing the minor cannabinoid CBG at this level of chromatographic purity.

The invention further provides a substantially pure preparation of cannabigerol (CBG) having a chromatographic purity of greater than 92%, more preferably greater than 94%, more preferably greater than 96% and most preferably greater than 97% by area normalisation of an HPLC profile. The preparation is preferably a clear colourless solution at room temperature.

The preparation typically comprises:
4% or less, more preferably 3% or less, and most preferably less than 2% CBD (w/w),
less than 1%, preferably less than 0.8%, more preferably less than 0.6%, more preferably less than 0.4%, more preferably less than 0.2% and most preferably less than 0.1% $\Delta^9$-THC (w/w),
less than 1%, preferably less than 0.8%, more preferably less than 0.6%, more preferably less than 0.4%, more preferably less than 0.2%, and most preferably less than 0.1% CBN (w/w).

The availability of such enriched extracts or substantially pure preparations will permit further evaluation of the pharmacology of CBG in order to assess its pharmaceutical potential. The enriched extract/substantially pure preparation is also useful as a reference standard in chromatographic characterisation of *cannabis*-derived medicines.

The preferred method of preparing enriched CBG extracts or substantially pure preparations of CBG from *cannabis* plant material comprises:
i) decarboxylating the *cannabis* plant material,
ii) preparing an extract of the decarboxylated *cannabis* plant material with hexane,
iii) filtering the resultant extract and removing solvent from filtrate by rotary evaporation to form an extract enriched in CBG,
iv) passing a solution of the resulting CBG enriched extract through a column packed with Sephadex-LH20™, eluting with 2:1 chloroform/dichloromethane,
v) collecting CBG rich fractions eluted from the column and removing solvent by rotary evaporation,
vi) re-dissolving the crude CBG obtained in step v) in methanol, removing insoluble residue by filtration and removing solvent from filtrate by rotary evaporation,
vii) re-dissolving the product of step vi) in pentane, removing insoluble residue by filtration and removing solvent from filtrate by rotary evaporation to produce a highly enriched CBG extract or substantially pure preparation of CBG.

The *cannabis* plant material will preferably be derived from *cannabis* plants having a relatively high CBG content.

Optionally a further step of flash chromatography may be conducted to further improve purity, preferably as set out in step viii) below. Such a step results in a further improvement in purity to greater than 99% (w/w). The skilled person will appreciate that an equivalent step could be used to improve purity for any of the other cannabinoids.

Step viii) loading the substantially pure cannabigerol or the cannabigerol enriched product onto a Chromabond Flash BT 12M silica cartridge column, eluting with hexam:ethyl acetate (98:2) at a flow rate of approximately 5 ml/min.

The invention still further comprises a product enriched in cannabichromene (CBC) having a chromatographic purity of greater than 80%, more preferably greater than 85% by area normalisation of an HPLC profile.

The product preferably comprises less than 5%, preferably less than 4%, more preferably less than 3%, more preferably less than 2% and most preferably 1% or less CBD (w/w),
less than 2%, preferably less than 1.5%, more preferably less than 1.0%, more preferably less than 0.5% and most preferably 0.3% or less $\Delta^9$ THC (w/w),
less than 1%, preferably less than 0.8%, more preferably less than 0.6%, more preferably less than 0.4%, more preferably less than 0.2% and most preferably 0.1% or less CBN (w/w).

Again, the inventors are the first to prepare *cannabis* plant extracts containing the minor cannabinoid CBC at this level of chromatographic purity.

The invention further provides a substantially ±5 pure preparation of cannabichromene (CBC) having a chromatographic purity of greater than 85%, more preferably greater than 90%, more preferably greater than 95%, more preferably greater than 98% and most preferably greater than 99% by area normalisation of an HPLC profile. The preparation is a clear colourless solution at room temperature.

The preparation typically comprises:
1% or less, more preferably 0.8% or less, more preferably 0.6% or less, more preferably 0.4% or less and most preferably less than 0.2% CBD (w/w),
less than 1%, preferably less than 0.8%, more preferably less than 0.6%, more preferably less than 0.4%, more preferably less than 0.2% and most preferably less than 0.1% $\Delta^9$-THC (w/w),
less than 1%, preferably less than 0.8%, more preferably less than 0.6%, more preferably less than 0.4%, more preferably less than 0.2% and most preferably less than 0.1% CBN (w/w).

The availability of such enriched extracts/substantially pure preparations will permit further evaluation of the pharmacology of CBC in order to assess its pharmaceutical potential. The enriched extract/substantially pure preparation is also useful as a reference standard in chromatographic characterisation of *cannabis*-derived medicines.

The preferred method for preparing enriched CBC extracts or substantially pure preparations of CBC from *cannabis* plant material comprises:
i) decarboxylating the *cannabis* plant material,
ii) preparing an extract of the decarboxylated *cannabis* plant material with hexane,
iii) filtering the resultant extract and removing solvent from filtrate by rotary evaporation to form an extract enriched in CBC,
iv) passing a solution of the resulting CBC enriched extract through a column packed with Sephadex-LH20™, eluting with 2:1 chloroform/dichloromethane,
v) collecting CBC rich fractions eluted from the column and removing solvent by rotary evaporation, vi) re-dissolving the crude CBC obtained in step v) in methanol, removing insoluble residue by filtration and removing solvent from filtrate by rotary evaporation, vii) re-dissolving the product of step vi) in pentane, removing insoluble residue by filtration and removing solvent from filtrate by rotary evaporation to produce a highly enriched CBC extract or substantially pure preparation.

The *cannabis* plant material will preferably be derived from *cannabis* plants having a relatively high CBC content.

The method may optionally include a further purification step of flash chromatography comprising viii) loading the substantially pure preparation of CBC or the product enriched in CBC onto a Chromabond Flash BT 12M silica cartridge column, eluting with hexane:ethyl acetate (98:2) at a flow rate of approximately 5 ml/min.

The invention will be further understood with reference to the following experimental examples, together with the accompanying Figures, in which:

FIG. 1 shows TLC a profile of crystalline $\Delta^9$ THCA, compared to starting material (from G1 *cannabis* chemovar) and CBD and $\Delta^9$ THC standards. Chromatographic conditions: SII G/UV$_{254}$, Mobile phase hexane:diethyl ether 80:20, double development, Visualisation 0.1% Fast Blue B salt in water. Standards: 1 mg/ml CBD (BN 10601/C) in MeOH 5 µl applied to TLC plate, 1 mg/ml $\Delta^9$ THC (BN 10601/B) in MeOH 5 µl applied to TLC plate. Samples: 1 mg/ml THCA starting material in MeOH 5 µl applied to TLC plate, 1 mg/ml crystalline THCA in MeOH 5 µl applied to TLC plate.

FIG. 2 shows HPLC profiles of purified $\Delta^9$ THCA (98% THCA, 1% THC), compared to starting material (from G1 *cannabis* chemovar; 72% THCA, 17% THC).

FIG. 3 shows TLC profile of crystalline CBDA, compared to starting material (from G5 *cannabis* chemovar) and CBD and $\Delta^9$ THC standards. Chromatographic conditions and standards as for FIG. 1. Samples: 1 mg/ml CBDA starting material in MeOH 5 µl applied to TLC plate, 1 mg/ml crystalline CBDA in MeOH 5 µl applied to TLC plate.

FIG. 4 shows HPLC profiles of crystalline CBDA (94% CBDA, 3% CBD), compared to starting material (from G5 *cannabis* chemovar; 72% CBDA, 14% CBD).

FIG. 5 shows an HPLC profile of a colourless solution of CBDA (from G5 *cannabis* chemovar).

FIG. 6 shows TLC profiles of purified $\Delta^9$ THC compared to BDS starting material and CBD and $\Delta^9$ THC standards. Chromatographic conditions and standards as for FIG. 1. Samples: 1 mg/ml $\Delta^9$ THC starting material in MeOH 5 µl applied to TLC plate, 1 mg/ml purified $\Delta^9$ THC in MeOH 5 µl applied to TLC plate.

FIG. 7 shows HPLC profiles of purified $\Delta^9$ THC (99.6% THC, 0% CBD) compared to starting material (BDS; 89% THC, 2% CBD).

FIG. 8 shows comparative HPLC profiles of purified $\Delta^9$ THC and commercially available $\Delta^9$ THC standard (Sigma; 95% THC, 4% CBN).

FIG. 9 shows GC profiles of purified $\Delta^9$ THC and starting material (BDS).

FIG. 10 shows TLC profiles of purified $\Delta^9$ THCV and THCV starting material (BDS) compared to CBD and $\Delta^9$ THC standards. Chromatographic conditions and standards as for FIG. 1. Samples: 1 mg/ml $\Delta^9$ THCV starting material in MeOH 5 µl applied to TLC plate, 1 mg/ml crystalline $\Delta^9$ THCV in MeOH 5 µl applied to TLC plate.

FIG. 11 shows HPLC profiles of $\Delta^9$ THCV and starting material (BDS).

FIG. 12 shows GC profiles of purified $\Delta^9$ THCV and starting material (BDS).

FIG. 13 shows TLC profiles of enriched CBG extract and starting material (BDS from G41 chemovar-decarboxylated) compared to CBD and $\Delta^9$ THC standards. Chromatographic conditions and standards as for FIG. 1. Samples: 1 mg/ml CBG starting material in MeOH 5 µl applied to TLC plate, 1 mg/ml enriched CBG extract in MeOH 5 µl applied to TLC plate.

FIG. 14 shows HPLC profiles of enriched CBG extract and starting material (BDS from G41 chemovar-decarboxylated).

FIG. 15 shows an HPLC profile of a colourless solution CBG preparation (from decarboxylated G41 *cannabis* chemovars).

FIG. 16 shows an HPLC profile of further flash chromatography purified CBG preparation compared to improved purity CBG (from decarboxylated G41 *cannabis* chemovars).

FIG. 17 shows GC profiles of enriched CBG extract and starting material (BDS from G41 chemovar-decarboxylated).

FIG. 18 shows TLC profiles of enriched CBC extract and starting material (BDS from G80 chemovar-decarboxylated) compared to CBD and $\Delta^9$ THC standards. Chromatographic conditions and standards as for FIG. 1. Samples: 1 mg/ml CBC starting material in MeOH 5 µl applied to TLC plate, 1 mg/ml purified enriched CBC extract in MeOH 5 µl applied to TLC plate.

FIG. 19 shows HPLC profiles of enriched CBC extract and starting material (BDS from G80 chemovar-decarboxylated).

FIG. 20 shows an HPLC profile of a colourless solution CBC preparation (from decarboxylated G80 *cannabis* chemovars).

FIG. 21 shows GC profiles of enriched CBC extract and starting material (BDS from G80 chemovar-decarboxylated).

EXAMPLES

Materials and Methods

Plant Material

GW Pharma Ltd has developed distinct varieties of *Cannabis* plant hybrids to maximise the output of the specific chemical constituents, cannabinoids. Various types of plant are used; one chemovar, designated G1 or "high THC" chemovar, produces >90% total cannabinoid content as $\Delta^9$ THC (naturally occurring in the plant in the form of $\Delta^9$ THCA) and a further chemovar, designated G5 or "high CBD" chemovar produces >90% total cannabinoid content as CBD (naturally occurring in the plant in the form of CBDA). Other chemovars yield significant amounts of the minor cannabinoids $\Delta^9$ THCV (G9 chemovar), CBG (G41 chemovar) and CBC (G80 chemovar). Alternative varieties can be obtained—see for example, Common cannabinoids phenotypes in 350 stocks of *cannabis*, Small and Beckstead, Lloydia vol 36b, 1973 p 144-156—and bred using techniques well known to the skilled man to maximise cannabinoid content.

Solvents

All solvents used in the isolation and analysis of the cannabinoids; n-pentane, hexane, chloroform, dichloromethane, di-ethyl ether, acetonitrile, water, methanol and glacial acetic acid were, unless otherwise stated, of chromatographic or A.R. grade.

Standards

Reference materials from Sigma were used as standards in the analysis of extracts, intermediates and finished products, these were: $\Delta^9$ THC in methanol BN 10601/B (ca. 1 mg/ml) and CBD in methanol BN 10601/C (ca. 1 mg/ml).

Solvent Extraction Step

For preparation of $\Delta^9$ THCA and CBDA samples of G1, THC *cannabis* chemovar (100 g) and G5, CBD *cannabis* chemovar (100 g) were extracted twice with 0.1% v/v glacial acetic acid in hexane (A.R. grade) at a solvent:herb ratio of 15:1. The resulting extracts were filtered and then solvent removed by rotary evaporation to yield crude extracts enriched in the respective cannabinoid acids and suitable for further processing.

For preparation of cannabigerol (CBG) and cannabichromene (CBC) samples of G41, CBG cannabis chemovar (100 g) and G80, CBC cannabis chemovar (100 g) were decarboxylated at 120° C. for 1 hour and then extracted twice with hexane at a solvent:herb ratio of 15:1. Following the removal of solvent, this yielded a crude extract enriched in the respective compounds CBG and CBC and suitable for further processing.

For preparation of $\Delta^9$ THC and $\Delta^9$ THCV ethanolic solutions of botanical drug substances were prepared, respectively, from high THC and high THCV cannabis chemovars according to the following process:

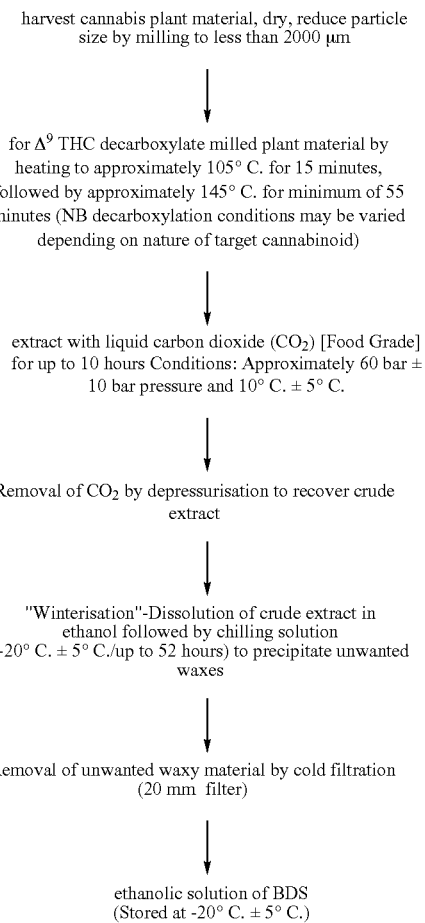

Extraction using liquid $CO_2$ is carried out under sub-critical conditions at a temperature of approximately 10° C.±5° C. using a pressure of approximately 60 bar±10 bar. Decarboxylated plant material is packed into a single column and exposed to liquid $CO_2$ under pressure for approximately 8 hours, $CO_2$ mass flow 1250 kg/hr±20%.

Following depressurisation and venting off of the $CO_2$ the crude BDS extract is collected into sealed vessels. The crude BDS extract is held at −20° C.±5° C.

The crude BDS extract contains waxes and long chain molecules. Removal is by "winterisation", whereby the crude BDS extract is warmed to e.g. 40° C.±4° C. to liquefy the material. Ethanol is added in the ratio of 2:1 ethanol volume to weight of crude BDS extract. The ethanolic solution is then cooled to −20° C.±5° C. and held at this temperature for approximately 48 hours.

On completion of the winterisation the precipitate is removed by cold filtration through a 20 μm filter, to give an ethanolic solution of the BDS.

Preliminary charcoal clean-up may be carried out by passing the ethanolic BDS solution (500 mg/ml) through a disposable plastic column (130 mm×27 mm i.d) packed with activated charcoal (decolourcarb DCL GDC grade, from Sutcliffe Speakman Carbons, 15.4 g per unit). Absolute ethanol B.P. (Hayman) is used as the solvent.

Ethanol and any water that may be present are removed by evaporation, e.g. rotary evaporation or thin film evaporation under reduced pressure (60° C.±2° C., with vapour at 40° C.±2° C./172 mbar and 72 mbar±4 mbar). The resulting product may be applied directly to the chromatography column.

Column Chromatography Step

Low pressure column chromatography separations were carried out using a glass column (length×internal diameter=1560 mm×24 mm), packed with Sephadex LH-20™ (Fluke). The column length:internal diameter ratio was therefore 65:1. A 2:1 chloroform/dichloromethane mixture was used as eluant. Eluate was collected as 50 ml fractions.

For purification of $\Delta^9$ THCA and CBDA approximately 20 ml of crude extract containing the equivalent of 100 g herb was applied to a glass column (dimensions: length 1560 mm×internal diameter 24 mm), packed with 400 g of Sephadex LH-20™ stationary phase, as described above. The qualitative composition of eluted fractions was monitored by TLC.

For the purification of $\Delta^9$ THC, 2.5 g of charcoal purified BDS (THC) extract was processed through the above low pressure chromatography system, (i.e. stationary phase:sample ratio of 160:1). Eluted fractions were analysed for $\Delta^9$ THC content by TLC.

For purification of CBG and CBC approximately 20 ml of crude extract containing the equivalent of 100 g herb was applied to a glass column (dimensions: length 1560 mm×internal diameter 24 mm), packed with 400 g of sephadex stationary phase.

For the purification of $\Delta^9$ THCV, 3 g of charcoal purified BDS (THCV) extract was processed through the above low pressure chromatography system, (i.e. stationary phase:sample ratio of 133:1).

Solvent Treatment Steps

Steps of re-dissolving extracts in the first and second solvents, filtering to remove insoluble material and removing solvent by rotary evaporation are carried out according to standard laboratory procedures, such as would be known to those skilled in the art.

TLC Analysis

The qualitative composition of fractions eluted from the chromatography column and other intermediates was monitored by TLC.

TLC uses both retention time and characteristic spot colour to effectively identify the cannabinoid/cannabinoid acid components in a complex mixture. Methanolic solutions of the fractions eluted from the chromatographic column are prepared for TLC analysis. An aliquot is spotted onto a TLC plate, alongside suitable reference samples (e.g. for at least $\Delta^9$ THC and CBD). Following exposure to Fast Blue B reagent, THC and THCA present as pink spots, while CBD and CBDA are orange in colour. Neutrals can be distinguished from the acids by comparison of the Rf value to that obtained for the standards. Identity is confirmed by comparison of Rf and colour of the sample spot, to that obtained for the appropriate standard.

A typical TLC protocol is as follows:
a) Materials and Methods
Equipment:
Application device capable of delivering an accurately controlled volume of solution i.e. 1 µl capillary pipette or micro liter syringe.
TLC development tank with lid
Hot air blower
Silica gel G TLC plates (SIL N-HR/UV$_{254}$), 200 µm layer with fluorescent indicator on polyester support.
Dipping tank for visualisation reagent.
Mobile phase 80% petroleum ether 60:80/20% Diethyl ether.
Visualisation reagent 0.1% w/v aqueous Fast Blue B salt BN (Sigma Corp) (100 mg in 100 ml de-ionised water). An optional method is to scan at UV 254 and 365 nm.
b) Sample preparation
i) Herbal raw material
Approximately 200 mg of finely ground, dried *cannabis* is weighed into a 10 ml volumetric flask. Make up to volume using methanol:chloroform (9:1) extraction solvent.
Extract by ultrasound for 15 minutes. Decant supernatant and use directly for chromatography.
ii) Eluted column fractions and intermediate extracts are dissolved in methanol then used directly. Suitable dilutions may be determined empirically.
iii) Final products
The final products (pure cannabinoids or enriched extracts) are dissolved in methanol to s suitable concentration (which may be determined empirically) then used directly for chromatography. All sample preparations should produce a final concentration of about 0.5 mg/ml.
iv) Botanical drug substance
Accurately weigh approximately 50 mg of botanical drug substance into a 25 ml volumetric flask. Dissolve to make volume with HPLC grade methanol.
c) Standards
0.1 mg/ml $\Delta^9$-THC in methanol (Sigma).
0.1 mg/ml CBD in methanol (Sigma).
The standard solutions are stored frozen at −20° C. between uses and are used for up to 12 months after initial preparation.
d) Test solutions and method
Apply to points separated by a minimum of 10 mm.
i) either 5 µl of herb extract or 1 µl of pure cannabinoid/enriched extract solution or 1 µl of diluted column eluate as appropriate,
ii) 5 µl of 0.1 mg/ml $\Delta^9$-THC in methanol standard solution,
iii) 5 µl of 0.1 mg/ml CBD in methanol standard solution.
Dry the prepared plate with a hot air blower.
Place the base of the TLC plate in a development tank containing the mobile phase and saturated with vapour.
Elute the TLC plate through a distance of 8 cm, then remove the plate. Allow solvent to evaporate from the plate and then repeat the elution for a second time (double development). Remove plate and allow it to dry in air.
The entire plate is briefly immersed in the Fast Blue B reagent until the characteristic red/orange colour of cannabinoids begins to develop. The plate is removed and allowed to dry under ambient conditions in the dark.
Cannabinoids will give an orange-purple colour:
Cannabidiol CBD orange (fastest running)
$\Delta^9$ Tetrahydrocannabinol THC pink
Cannabinol CBN purple
Cannabichromene CBC pink purple
Cannabigerol CBG orange
$\Delta^9$ tetrahydrocannabivarin THCV purple The corresponding acids form streaks of the same colour as the neutral component spots. The acids run at lower $R_f$.

HPLC Analysis

The composition of the isolated products may be determined by HPLC analysis.

A typical HPLC assay for $\Delta^9$ THC, $\Delta^9$ THCA, CBD, CBDA and CBN may be carried out as follows:
a) Materials and Methods
Chromatography Equipment and conditions:
Equipment Agilent (HP)1100 HPLC system with variable wavelength UV detector or diode array detector.
HPLC Column Discovery C8 5 µm 15 cm×0.46 cm
Pre-Column Kingsorb C18 5 µm 3 cm×0.46 cm
Mobile Phase Acetonitrile:Methanol:0.25% w/v acetic acid (16:7:6 by volume)
Column Temp 25° C.
Flow Rate 1.0 ml min-1
Detection 220 nm 600 mA f.s.d. Second wavelength 310 nm
Injection Volume 10 µl
Run Time 20-25 minutes (may be extended for samples containing small amount of late-eluting peaks)
Elution Order CBD, CBDA, $\Delta^9$ THCV, CBN, $\Delta^9$ THC, CBC, $\Delta^9$ THCA
b) Sample Preparation
Samples of "pure" cannabinoids/cannabinoid acids and enriched extracts are diluted in methanol prior to HPLC analysis. Optimal dilutions may be determined empirically.

Herbal *cannabis* samples are prepared by taking a 100 mg sample and treating this with 5 or 10 ml of Methanol/Chloroform (9/1 w/v). The dispersion is sonicated in a sealed tube for 10 minutes, allowed to cool and an aliquot is centrifuged and suitably diluted with methanol prior to chromatography.
c) Standards
Stock standard solutions of CBD, CBN and $\Delta^9$ THC in methanol at approximately 1 mg ml-1 are stored at −20° C. Diluted working standards (0.1 mg/ml for $\Delta^9$ THC and CBD and 0.01 mg/ml for CBN) are prepared in methanol from the stock standards and stored at −20° C. (maximum period of twelve months after initial preparation). After preparation, standard solutions must be aliquoted into vials to reduce the amount of standard exposed to room temperature. Prior to use in an HPLC sample assay, the required number of standard vials are removed and allowed to equilibrate to room temperature.

Injection of each standard is made in triplicate prior to the injection of any test solution. At suitable intervals during the processing of test solutions, repeat injections of standards are made. In the absence of reliable CBDA and $\Delta^9$ THCA standards, these compounds are analysed using respectively the CBD and $\Delta^9$ THC standard response factors.
d) Test Solutions
Diluted test solutions are made up in methanol and should contain analytes in the linear working range of from 0.02-0.2 mg/ml.
e) Chromatography Acceptance Criteria:
The following acceptance criteria are applied to the results of each sequence as they have been found to result in adequate resolution of all analytes (including the two most closely eluting analytes CBD and CBDA)

TABLE 1

Retention time windows and Relative Retention
Time (RRT) to $\Delta^9$ THC for each analyte

| Cannabinoid | Retention time (minutes) | RRT (THC) |
|---|---|---|
| CBD | 5.1-5.8 | 0.58 |
| CBN | 7.4-8.3 | 0.83 |
| $\Delta^9$ THC | 9.0-10.0 | 1.00 |
| CBDA | 5.5-6.2 | 0.615 |
| $\Delta^9$ THCV | 5.9-6.2 | 0.645 |
| CBC | 11.6-12.8 | 1.30 |
| $\Delta^9$ THCA | 14.6-16.0 | 1.605 |

TABLE 2

Peak Shape (Symmetry Factor according to
British Pharmacopoeia method)

| Cannabinoid | Symmetry factor |
|---|---|
| CBD | <1.30 |
| CBN | <1.25 |
| $\Delta^9$ THC | <1.35 | f) Data Processing

Cannabinoids can be subdivided into neutral and acidic—the qualitative identification can be performed using the DAD dual wavelength mode. Acidic cannabinoids absorb strongly in the region of 220 nm-310 nm. Neutral cannabinoids only absorb strongly in the region of 220 nm.

Routinely, only the data recorded at 220 nm is used for quantitative analysis.

The DAD can also be set up to take UV spectral scans of each peak, which can then be stored in a spectral library and used for identification purposes.

Data processing for quantitation utilises batch processing software on the Hewlett Packard Chemstation.

g) Calculation:

Chromatographic purity of cannabinoid samples is calculated as a % of total cannabinoid content by area normalization.

Capillary Gas Chromatography (GC) Analysis a) Chromatography equipment and conditions Equipment Agilent (HP) 5890 or 6890 GLC system with HP7673 Autosampler and FID detector GLC column SE54(EC5) 30 m×0.32 mm i.d. (Alltech) phase thickness 0.25 μm Flow rate Constant pressure (10.3 psi). Normal initial flow rate 34 cm sec$^{-1}$ (2.0 ml min$^{-1}$)

Column oven 70° C. initially then ramp 5° C. min$^{-1}$ to 250° C. Hold at 250° C. for 15 minutes.

Injector temp 250° C.

Detector temp 325° C.

Injection Vol 1 μl, split ratio 2.5:1

Run time 45 minutes

Fuel gases Hydrogen 40 ml min$^{-1}$
  Air 450 ml min$^{-1}$
  Helium 45 ml min$^{-1}$ b) Standard Preparation Stock standard solutions of CBD, CBN and $\Delta^9$ THC in methanol at approximately 1 mg ml-1 are stored at −20° C. Diluted working standards (0.1 mg/ml for $\Delta^9$ THC and CBD and 0.01 mg/ml for CBN) are prepared in methanol from the stock standards and stored at −20° C. (maximum period of twelve months after initial preparation). Allow an aliquot pipetted into an autosampler vial to equilibrate to room temperature prior to use in a GC assay.

c) Sample Preparation

Samples of final products, i.e. "pure" cannabinoids/cannabinoid acids and enriched extracts are diluted in methanol prior to HPLC analysis. Optimal dilutions may be determined empirically.

*Cannabis* plant material samples are prepared by taking 100 mg chopped dried material and treating this with 5 or 10 ml of Methanol/Chloroform (9:1 v/v). Extract the sample in an ultrasonic bath for 15 minutes and allow to stand in the dark for 18 hours.

d) Chromatography Procedure

Standard solutions are used to provide quantitative and retention time data. These can be typically injected in triplicate prior to the injection of any sample solutions and then singularly at suitable intervals during the run, with a maximum of 10 test samples in between standards.

TABLE 3

| | Retention times |
|---|---|
| THCV | 33.7-34.5 minutes |
| CBD | 35.6-36.3 minutes |
| $\Delta^9$ THC | 37.2-38.1 minutes |
| CBN | 38.5-39.1 minutes |

Example 1

Preparation of $\Delta^9$ THCA

Summary of Process:

Extract THC herb (G1 chemovar) with 0.1% v/v acetic acid in hexane.

↓

Filter and remove solvent from filtrate on rotary evaporator.

↓

Pass a solution of the resulting THCA enriched extract through a column packed with Sephadex LH20, eluting with 2:1 chloroform/dichloromethane.

↓

Collect THCA rich fractions and remove solvent by rotary evaporation.

↓

Re-dissolve crude THCA in methanol and remove insoluble residue by filtration.

↓

Remove solvent from filtrate by rotary evaporation.

↓

-continued

Re-dissolve crude THCA in pentane and remove insoluble residue by filtration.

↓

Remove solvent from filtrate by rotary evaporation.

↓

$\Delta^9$ THCA crystals

Results:

Yield:

100 g of G1 chemovar yields approx 5 g of purified $\Delta^9$ THCA

Characteristics:

Pale yellow crystalline solid.
Chromatographic purity=98% by area normalization.
CBD<0.5% w/w
THC=1.0% w/w
CBN<1.0% w/w
Melting point=70° C. (with decomposition).
Material slowly decarboxylates in solution $\Delta^9$THCA→$\Delta^9$THC+$CO_2$ Example 2

Preparation of CBDA

Summary of Process:

Extract CBD herb (G5 chemovar) with 0.1% v/v acetic acid in hexane.

↓

Filter and remove solvent from filtrate on rotary evaporator.

↓

Pass a solution of the resulting CBDA enriched extract through a column packed with Sephadex LH20, eluting with 2:1 chloroform/dichloromethane.

↓

Collect CBDA rich fractions and remove solvent by rotary evaporation.

↓

Re-dissolve crude CBDA in methanol and remove insoluble residue by filtration.

↓

Remove solvent from filtrate by rotary evaporation.

↓

-continued

Re-dissolve crude CBDA in pentane and remove insoluble residue by filtration.

↓

Remove solvent from filtrate by rotary evaporation.

↓ i) CBDA crystals or ii) CBDA solution

For i) above:

Yield:

100 g of G5 chemovar yields approx 5 g of purified CBDA.

Characteristics:

Pale yellow crystalline solid
Melting Point=45-48° C.
Chromatographic purity=94% CBDA by area normalisation with reference to FIG. 4
*CBD 3%.
THCA non detected i.e. <0.1%
THC non detected i.e. <0.1%
Material slowly decarboxylates in solution

CBDA→CBD+$CO_2$

* As CBDA does not co-elute with CBD during processing of the extract in the low pressure column chromatography method employed, the detected CBD is likely to be formed from the breakdown of the CBDA during processing and analysis. This undesirable decarboxylation of the purified material might be minimised by manipulation of CBDA at sub-ambient temperatures.

For ii) above:

Characteristics:

Clear colourless solution
Chromatographic purity=98.9% CBDA by area normalisation with reference to FIG. 5
THCA 0.28%

Example 3

Preparation of $\Delta^9$ THC

Summary of Process:

Ethanolic solution of BDS (approx 400 mg/ml) passed through a column of activated charcoal, and eluate collected.

↓

Remove solvent by rotary evaporation to give THC enriched fraction.

↓

Pass a solution of the resulting THC enriched extract through a column packed with Sephadex LH20, eluting with 2:1 chloroform/dichloromethane.

↓

-continued

Collect THC rich fractions and remove solvent by rotary evaporation.

↓

Re-dissolve crude THC in methanol and remove insoluble residue by filtration.

↓

Remove solvent from filtrate by rotary evaporation.

↓

Re-dissolve crude THC in pentane and remove insoluble residue by filtration.

↓

Remove solvent from filtrate by rotary evaporation.

↓

$\Delta^9$ THC SEMI-SOLID

Yield:
 3.5 g of $\Delta^9$ THC BDS yields approx 1.5 g of purified $\Delta^9$ THC.

Characteristics:
 Clear semi-solid which rapidly takes on a purple colour when exposed to air.
 (This colour change is reversible when the material is redissolved in a suitable solvent).
 Chromatographic purity>99% $\Delta^9$ THC by area normalization.
 Chromatographic purity superior to commercially available $\Delta^9$ THC Sigma standard
 CBD non detected i.e. <0.1%
 CBN non detected i.e. <0.1%
 Identity confirmed by HPLC, GC and TLC retention behaviour compared to $\Delta^9$ THC Sigma standard.

Example 4

Preparation of $\Delta^9$ THCV

Summary of Process:

Ethanolic solution of BDS, derived from G9 chemovar, passed through column of activated charcoal, and eluate collected.

↓

Remove solvent by rotary evaporation to give enriched cannabinoid extract.

↓

Pass a solution of the resulting concentrated extract through a column packed with Sephadex LH20 and eluting with 2:1 chloroform/dichloromethane.

↓

-continued

Collect THCV rich fractions and remove solvent by rotary evaporation.

↓

Re-dissolve crude THCV enriched fractions in methanol and remove insoluble residue by filtration.

↓

Remove solvent from filtrate by rotary evaporation.

↓

Re-dissolve crude THCV enriched fractions in pentane and remove insoluble residue by filtration.

↓

Remove solvent from filtrate by rotary evaporation.

↓

Crystalline THCV

Yield:
 4.0 g of $\Delta^9$ THCV. BDS yields approx 1.3 g of purified $\Delta^9$ THCV.

Characteristics:
 Off white crystals which rapidly take on a purple colour when exposed to air. This colour change is reversible when the crystals are redissolved.
 Chromatographic purity >99% by area normalization.
 CBD non detected i.e. <0.1%
 THC 0.5%
 CBN non detected i.e. <0.1%
 Superior to BDS THCV, which contains 75% THCV & 17% THC as % of total cannabinoids, for studies of chemistry and pharmacology of THCV.
 Identity confirmed by HPLC & GC retention times versus THCV fraction previously authenticated by GC-MS.

Example 5

Preparation of Cannabigerol (CBG)

Summary of Process:

Extract decarboxylated G41 chemovar with hexane.

↓

Filter and remove solvent from filtrate on rotary evaporator.

↓

Pass a solution of the resulting concentrated extract through a column packed with Sephadex LH20 and eluting with 2:1 chloroform/dichloromethane.

↓

-continued

Collect CBG rich fractions and remove solvent by rotary evaporation.

↓

Re-dissolve crude CBG enriched fractions in methanol and remove insoluble residue by filtration.

↓

Remove solvent from filtrate by rotary evaporation.

↓

Re-dissolve crude CBG enriched fraction in pentane and remove insoluble residue by filtration.

↓

Remove solvent from filtrate by rotary evaporation.

↓ i) Highly enriched CBG extract or ii) CBG solution

↓

Flash chromatography

For i) above:
Yield:
  100 g of G41 chemovar yields approx 300 mg of CBG enriched fraction.
Characteristics:
  Orange/yellow semi-solid.
  Identification by GC retention index relative to THC & CBD standards [ref: Brenneisen, R. & El Sohly, M. A., "Chromatographic & spectroscopic Profiles of *Cannabis* of Different Origins: Part I," Journal of Forensic Sciences, JFSCA, vol. 33, No. 6, pp. 1385-1404, 1988].
  Chromatographic purity >92% by area normalization with reference to FIG. 14.
  CBD non-detected i.e. <0.1%
  THC 0.1%
  CBN non-detected i.e. <0.1%
For ii) above:
Characteristics:
  Clear colourless solution
  Chromatographic purity=97.2% CBG by area normalisation with reference to FIG. 15
  CBD 1.66%
  CBN non-detected i.e. <0.1%
Following flash chromatography of product ii):
Characteristics:
  Clear colourless solution
Chromatographic purity-99.9% CBG by area normalisation with reference to FIG. 16.

Example 6

Preparation of Cannabichromene (CBC)

Summary of Process:

Extract decarboxylated G80 chemovar with hexane.

↓

Filter and remove solvent from filtrate on rotary evaporator.

↓

Pass a solution of the resulting concentrated extract through a column packed with Sephadex LH20 and eluting with 2:1 chloroform/dichloromethane.

↓

Collect CBC rich fractions and remove solvent by rotary evaporation.

↓

Re-dissolve crude CBC enriched fractions in methanol and remove insoluble residue by filtration.

↓

Remove solvent from filtrate by rotary evaporation.

↓

Re-dissolve crude CBC enriched fractions in pentane and remove insoluble residue by filtration.

↓

Remove solvent from filtrate by rotary evaporation.

↓ i) Highly enriched CBC extract or ii) CBC solution

For i) above:
Yield:
  100 g of G80 chemovar yields approx 300 mg of CBC enriched fraction.
Characteristics:
  Orange/yellow semi-solid.
  Identification by GC retention index relative to THC & CBD standards [ref: Brenneisen, R. & El Sohly, M. A., "Chromatographic & spectroscopic Profiles of *Cannabis* of Different Origins: Part I," Journal of Forensic Sciences, JFSCA, vol. 33, No. 6, pp. 1385-1404, 1988].
  Chromatographic purity >85% by area normalization with reference to FIG. 19.
  CBD 1.0%
  THC 0.3%
  CBN 0.1%

For ii) above:
Characteristics:
  Clear colourless solution
  Chromatographic purity=99.6% CBC by area normalisation with reference to FIG. 20
    CBD 0.12%
    CBN 0.09%

The invention claimed is:

1. A botanical drug substance (BDS) derived from *cannabis* plants having a tetrahydrocannabivarin (THCV) content of greater than 70% of total cannabinoids with delta 9 tetrahydrocannabinol (delta 9 THC) being reduced to a level of a minor constituent, which BDS has been obtained by extraction with carbon dioxide followed by a secondary extraction to remove a substantial proportion of non-cannabinoid materials including a substantial proportion of waxes, wax esters and glycerides, unsaturated fatty acid residues, terpenes, carotenes, and flavonoids, and in which the THCV content has been further enriched by separation or fractionation of cannabinoids other than THC, and wherein the delta 9 THC content is less than 2.0% of total cannabinoids.

2. A botanical drug substance as claimed in claim 1 wherein the THCV is delta 9 THCV.

3. A botanical drug substance as claimed in claim 1, wherein the extraction with carbon dioxide is extraction with subcritical carbon dioxide.

4. A botanical drug substance (BDS) as claimed in claim 1, wherein the secondary extraction comprises "winterisation".

5. A botanical drug substance as claimed in claim 1 wherein the BDS is obtained by a method comprising the following steps:
  i) Harvesting and decarboxylating *cannabis* plant material;
  ii) Extraction with liquid carbon dioxide (CO2), and removal of CO2 to recover a crude extract;
  iii) Dissolution of the crude extract in ethanol followed by chilling of the solution to precipitate unwanted waxes; and
  iv) Removal of unwanted waxy material by cold filtration.

6. A botanical drug substance as claimed in claim 1 characterized in that it exhibits an HPLC profile as shown in FIG. 11 (top panel) with a THCV peak at a retention time of 5.9 to 6.2 minutes and a THC peak at a retention time of 9.0 to 10.0 minutes.

7. A botanical drug substance as claimed in claim 1 characterized in that it exhibits a GC profile as shown in FIG. 12 (top panel) with a THCV peak at a retention time of 33.7 to 34.5 minutes and a THC peak at a retention time of 37.2 to 38.1 minutes.

8. A botanical drug substance as claimed in claim 1 comprising at least 75% THCV and less than 2.0% THC of total cannabinoids.

9. A botanical drug substance as claimed in claim 1 comprising a THCV content of greater than 95% of total cannabinoids.

10. A botanical drug substance as claimed in claim 1 comprising less than 1.5%, 1.0% or 0.5% delta 9 THC of total cannabinoids.

11. A botanical drug substance as claimed in claim 1 comprising less than 1.0%, 0.8%, 0.6%, 0.4%, 0.2% or 0.1% cannabidiol (CBD) of total cannabinoids.

12. A botanical drug substance as claimed in claim 1 comprising less than 1.0%, 0.8%, 0.6%, 0.4%, 0.2% or 0.1% cannabinol (CBN).

* * * * *

UNITED STATES PATENT AND TRADEMARK OFFICE
CERTIFICATE OF CORRECTION

| | | |
|---|---|---|
| PATENT NO. | : 8,846,409 B2 | Page 1 of 1 |
| APPLICATION NO. | : 12/714907 | |
| DATED | : September 30, 2014 | |
| INVENTOR(S) | : Flockhart et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 516 days.

Signed and Sealed this
Twenty-fifth Day of August, 2015

Michelle K. Lee
*Director of the United States Patent and Trademark Office*